United States Patent
Zhang et al.

(10) Patent No.: US 9,605,280 B2
(45) Date of Patent: *Mar. 28, 2017

(54) ESCHERICHIA COLI CONTAINING MUTATED LPDA GENE AND APPLICATION THEREOF

(71) Applicant: Tianjin Institute of Industrial Biotechnology, Chinese Academy of Sciences, Tianjin (CN)

(72) Inventors: Xueli Zhang, Tianjin (CN); Xinna Zhu, Tianjin (CN); Jing Chen, Tianjin (CN)

(73) Assignee: TIANJIN INSTITUTE OF INDUSTRIAL BIOTECHNOLOGY, CHINESE ACADEMY OF SCIENCES, Tianjin (CN)

(*) Notice: Subject to any disclaimer, the term of this patent is extended or adjusted under 35 U.S.C. 154(b) by 0 days.

This patent is subject to a terminal disclaimer.

(21) Appl. No.: 14/891,782

(22) PCT Filed: May 23, 2014

(86) PCT No.: PCT/CN2014/078265
§ 371 (c)(1),
(2) Date: Nov. 17, 2015

(87) PCT Pub. No.: WO2014/187355
PCT Pub. Date: Nov. 27, 2014

(65) Prior Publication Data
US 2016/0145648 A1   May 26, 2016

(30) Foreign Application Priority Data

May 24, 2013 (CN) .......................... 2013 1 0198769

(51) Int. Cl.
| | | |
|---|---|---|
| C12P 7/46 | (2006.01) |
| C12P 7/06 | (2006.01) |
| C12N 1/20 | (2006.01) |
| C12P 19/34 | (2006.01) |
| C12N 15/87 | (2006.01) |
| C12N 15/74 | (2006.01) |
| C12N 9/02 | (2006.01) |
| C12N 15/70 | (2006.01) |

(52) U.S. Cl.
CPC ............ *C12P 7/065* (2013.01); *C12N 9/0051* (2013.01); *C12N 15/70* (2013.01); *C12P 7/06* (2013.01); *C12P 7/46* (2013.01); *Y02E 50/17* (2013.01)

(58) Field of Classification Search
CPC .... C12P 7/06; C12P 7/46; C12P 7/065; C12N 9/0051; C12N 15/70; Y02E 50/17; Y02P 20/52
USPC ......... 435/145, 161, 252.33, 91.1, 463, 471, 435/476, 488; 536/23.1, 23.2; 530/350
See application file for complete search history.

(56) References Cited

U.S. PATENT DOCUMENTS

2014/0235815 A1* 8/2014 Burgard ................. C07C 55/10
528/271
2016/0097064 A1* 4/2016 Zhang .................. C12N 9/0051
435/145

FOREIGN PATENT DOCUMENTS

| CN | 101023178 A | 8/2007 |
| CN | 101128577 A | 2/2008 |
| CN | 102174455 A | 9/2011 |
| CN | 102803470 A | 11/2012 |
| RU | 2466186 C2 | 11/2012 |
| WO | WO 2009/062190 A2 | 5/2009 |
| WO | WO 2014/187357 A1 | 11/2014 |

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Datsenko et al., "One-step inactivation of chromosomal genes in *Escherichia coli* K-12 using PCR products" PNAS vol. 97, No. 12, pp. 6640-6645, Jun. 6, 2000.
Hong et al., "Research Progress on Metabolic Engineering of *Escherichia coli* 1-13 Strains for Ethanol Production", Journal of Agricultural Science and Technology, No. 4, vol. 11, Aug. 15, 2009, pp. 29-33 (with Eng. Abstract).
International Search Report mailed Sep. 3, 2014 in PCT/CN2014/078284.
International Search Report mailed Aug. 13, 2014 in PCT/CN2014/078265.
Jantama et al., "Combining Metabolic Engineering and Metabolic Evolution to Develop Nonrecombinant Strains of *Escherichia coli* C That Produce Succinate and Malate", Biotechnology and Bioengineering vol. 99, No. 5, Apr. 1, 2008, 1140-1153.

(Continued)

*Primary Examiner* — Ganapathirama Raghu
(74) *Attorney, Agent, or Firm* — Swanson & Bratschun, L.L.C.

(57) ABSTRACT

The invention relates to the field of modifying *E. coli* through genetic engineering. Specifically, the invention provides an *E. coli* containing a mutated lpdA gene. The invention also relates to use of the *E. coli* in the production of chemical material such as ethanol, and succinate etc. The invention also provides a method of producing chemical materials such as ethanol and succinate etc. by using the *E. coli*, as well as a method for increasing the activity of pyruvate dehydrogenase in *E. coli* by introducing a mutated lpdA gene.

10 Claims, 5 Drawing Sheets

(56) References Cited

OTHER PUBLICATIONS

Jantama et al., "Eliminating Side Products and Increasing Succinate Yield in in Engineered Strains of *E. coli* C", Biotechnology and Bioengineering vol. 101, No. 5, Dec. 1, 2008, 881-893.

Kim et al., "Construction of an *Escherichia coli* K-12 Mutant for Homoethanologenic Fermentation of Glucose or Xylose without Foreign Genes" Applied and Environmental Microbiology, vol. 73, No. 6, Mar. 2007, pp. 1766-1771.

Kim et al., "Dihydrolipoamide Dehydrogenase Mutation Alters the NADH Sensitivity of 1-13 Pyruvate Dehydrogenase Complex of *Escherichia coli* K-12", Journal of Bacteriology, No. 11, vol. 190, Jun. 2008, pp. 3851-3858.

Lee et al., "Metabolic Engineering of *Escherichia coli* for Enhanced Production of Succinic Acid, Based on Genome Comparison and in Silico Gene Knockout Simulation" Appl. Environ. Microbiol. 2005, 71(12):7880-7887.

Lu et al. "Combinatorial modulation of galP and glk gene expression for improved alternative glucose utilization", Appl Microbiol Biotechnol. DOI 10.1007/s00253-011-3752-y, Publication online Dec. 13, 2011.

Sanchez et al., "Novel pathway engineering design of the anaerobic central metabolic pathway in *Escherichia coli* to increase succinate yield and productivity", Metabolic Engineering (2005) 7:229-239.

Scholten et al. "Continuous cultivation approach for fermentative succinic acid production from crude glycerol by Basfia succiniciproducens DD1", Biotechnol Lett (2009) 31:1947-1951.

Tan et al., "Activating Phosphoenolpyruvate Carboxylase and Phosphoenolpyruvate Carboxykinase in Combination for Improvement of Succinate Production", Applied and Environmental Microbiology Aug. 2013 vol. 79, No. 16, p. 4838-4844.

Vemuri et al., "Effects of Growth Mode and Pyruvate Carboxylase on Succinic Acid Production by Metabolically Engineered Strains of *Escherichia coli*", Appl. Environ. Microbiol. 2002, 68(4):1715-1727.

Wilkinson et al., "NADH Inhibition and NAD Activation of *Escherichia coli* Lipoamide Dehydrogenase Catalyzing the NADH-Lipoamide Reaction*", The Journal of Biological Chemistry, No. 256, vol. 5, Mar. 10, 1981, pp. 2307-2314.

Wu et al., "Research Progress on Fiber Hydrolyzate Fermentation Production of Succinate", Food and Fermentation Industries, vol. 38, No. 9, Sep. 30, 2012 (with Eng Abstract).

Zhang et al., "Metabolic evolution of energy-conserving pathways for succinate production in *Escherichia coli*" PNAS Dec. 1, 2009. vol. 106. No. 48, p. 20180-20185.

Zhang et al., "Reengineering *Escherichia coli* for Succinate Production in Mineral Salts Medium", Applied and Environmental Microbiology, Dec. 2009, vol. 75, No. 24, p. 7807-7813.

Zhao et al., "Engineering central metabolic modules of *Escherichia coli* for improving b-carotene production" Metabolic Engineering, http://dx.doi.org/10.1016/j.ymben.2013.02.002 Feb. 2, 2013.

Zhou et al., "Engineering a native homoethanol pathway in *Escherichia coli* B for ethanol production", Biotechnol Lett (2008) 30:335-342.

Zhu et al. "Metabolic evolution of two reducing equivalent-conserving pathways for high-yield succinate production in *Escherichia coli*", Metabolic Engineering (2014) 24:87-96.

* cited by examiner

Figure 4A

Figure 4B

ESCHERICHIA COLI CONTAINING MUTATED LPDA GENE AND APPLICATION THEREOF

RELATED APPLICATIONS

This application is a 35 U.S.C. §371 national phase application of PCT/CN2014/078265 (WO 2014/187355) filed on May 23, 2014, entitled "ESCHERICHIA COLI CONTAINING MUTATED LPDA GENE AND APPLICATION THEREOF", which application claims the benefit of Chinese Application No. 201310198769.4, filed May 24, 2013, which is incorporated herein by reference in its entirety.

FIELD OF THE INVENTION

The invention relates to the field of genetically modifying E. coli. Specifically, the invention provides a recombinant E. coli containing a mutated lpdA gene. The invention also relates to use of the E. coli in the production of chemical materials such as ethanol, succinate, butanol, and 1,3-propanediol. The invention also provides a method of producing chemical materials such as ethanol and succinate by using the E. coli, as well as a method for increasing the activity of pyruvate dehydrogenase in E. coli by introducing a mutated lpdA gene.

Incorporated by reference herein in its entirety is the Sequence Listing entitled "Sequence listing.txt", created Nov. 11, 2015, size of 32 kilobytes.

BACKGROUND OF THE INVENTION

Great progresses have been recently achieved to produce chemical materials (such as ethanol, succinate etc.) by microbial fermentation. Compared to traditional petrochemical process, microbial fermentation has many advantages including high productivity, low cost, and the use of renewable raw materials instead of petrochemicals.

In microbial fermentation, E. coli is the most commonly used host for obtaining high-producing strain since it has clear physiological and genetic characteristic and can be genetically modified easily. E. coli also grows fast and can be cultured easily. Under anaerobic fermentation, E. coli generally consumes saccharides or their derivatives and produces mix-acids including formate, acetate, lactate, succinate, ethanol etc. For the strains of wild-type E. coli, the yield of ethanol and succinate is low. Recombinant DNA technology of microbial strains has been developed, which has been applied to modify specific enzymes involved in metabolic pathways of E. coli, for obtaining high-producing strains.

Pyruvate dehydrogenase complex (PDH), a complex of three enzymes, plays an important role in metabolic pathways of E. coli, catalyzing the irreversible oxidative decarboxylation of pyruvate to acetyl-CoA with reducing $NAD^+$ into NADH. Acetyl-CoA produced in this reaction go through tricarboxylic acid cycle (TCA) to perform cellular respiration. Pyruvate dehydrogenase complex establishes a connection between glycolysis metabolic pathway and TCA. Pyruvate decarboxylation is also called "pyruvate dehydrogenation", because of involving oxidization of pyruvate (Hansen et al., 1996 Biochim Biophys Acta 122: 355-358; Bisswanger 1981 J Biol Chem 256: 815-822; Quail et al., 1994 J Mol Microbiol 12:95-104).

During microbial anaerobic fermentation, $NAD^+$ and NADH are important co-factors for maintaining oxidation-reduction reactions. In this process, $NAD^+$ is key electron acceptor, and NADH as co-factor determines the supply of reducing equivalent in electron transfer (Garrigues et al., 1997 J Bacteriol 179: 5282-5287; Cassey et al., 1998 FEMS Microbiol Lett 159:325-329). During glycolysis, one molecule glucose generates two molecules NADH, while one molecule glucose can generate two molecules acetyl-CoA by pyruvate decarboxylation, with four molecules NADH generated (glucose→2 acetyl-CoA→4 NADH). Two more molecules NADH are generated in conversing pyruvate to acetyl-CoA than that of pyruvate into formate, producing additional reducing equivalent. Therefore, the activity of pyruvate dehydrogenase (PDH) in pyruvate decarboxylation is significant for increasing the supply of reducing equivalent in metabolic pathways.

PDH is the important enzyme connecting glycolysis and TCA, and its activity is low under anaerobic conditions although is high under aerobic conditions. The activity of PDH is inhibited by the acetyl-CoA and NADH produced by PDH reaction. NADH is an important reducing equivalent for microbial cell-factories, but NADH of high concentration inhibits PDH, making it as a critical rate-limiting enzyme in metabolic pathways. Kim (Kim et al., 2008 J Bacteriol 190: 3851-3858) isolated a mutant strain E354K (lpd101), whose dihydrolipoamide dehydrogenase (LPD) of PDH was mutated, which was identified to be responsible for reducing sensitivity of PDH to NADH under anaerobic conditions, increasing ethanol production by this pathway. Zhou et al. (Zhou et al., 2008 Biotechnol Lett 30:335-342) increased PDH the activity by introducing lpd mutation and the regulating aceEF gene, increasing the biomass and the yield of stain in fermentation processes.

In order to improve the titer and/or yield of E. coli in the production of chemical materials, it is desired to further modify the metabolic pathways of E. coli.

SUMMARY OF THE INVENTION

In one aspect, the invention provides an engineered recombinant E. coli.

In one embodiment, the invention provides a recombinant E. coli containing a mutated lpdA gene, wherein the polypeptide encoded by the mutated lpdA gene comprises modification(s) at one or more positions corresponding to the positions T81, P275, and A358 of the amino acid sequence shown in SEQ ID No.: 1, wherein the corresponding positions are determined by aligning the sequence of the polypeptide with SEQ ID No.: 1, and optionally at the position corresponding to T81, T is replaced with I, at the position corresponding to P275, P is replaced with S, and at the position corresponding to A358, A is replaced with V. In one preferred embodiment, in the E. coli, the expression of said mutated lpdA gene is enhanced, and/or the activity of protein encoded by said mutated lpdA gene is enhanced.

In one embodiment, the invention provides an E. coli comprising a mutated lpdA gene, wherein said mutated lpdA gene comprises modifications at one or more positions corresponding to the positions C242, C823, and C1073 of the nucleotide sequence shown in SEQ ID No.: 2, wherein the corresponding positions are determined by aligning the sequence of the gene with SEQ ID No.: 2, and optionally said mutations all are the replacement of C with T. In one preferred embodiment, in the E. coli, the expression of said mutated lpdA gene is enhanced, and/or the activity of protein encoded by said mutated lpdA gene is enhanced.

In one embodiment, the invention provides an E. coli comprising a mutated lpdA gene, wherein the polypeptide encoded by said mutated lpdA gene comprises a modification at the position corresponding to position A358 of the amino acid sequence shown in SEQ ID No.: 1, and optionally the modification at the position corresponding to A358 is the replacement of A with V.

In one embodiment, the invention provides an *E. coli* comprising a mutated lpdA gene, wherein the polypeptide encoded by said mutated lpdA gene comprises a modification at the position corresponding to position C1073 of the amino acid sequence shown in SEQ ID No.: 1, and optionally said modification is the replacement of C with T.

In one embodiment, the invention provides an *E. coli* comprising a mutated lpdA gene, wherein the polypeptide encoded by said mutated lpdA gene comprises modifications at the positions corresponding to positions T81, P275, and A358 of the amino acid sequence shown in SEQ ID No.: 1, and optionally wherein at the position corresponding to T81, T is replaced with I, at the position corresponding to P275, P is replaced with S, and at the position corresponding to A358, A is replaced with V.

In one embodiment, the invention provides an *E. coli* comprising a mutated lpdA gene, wherein said mutated lpdA gene comprises modifications at the positions corresponding to positions C242, C823, and C1073 of the nucleotide sequence shown in SEQ ID No.: 2, and optionally said mutations all are the replacement of C with T.

In a preferred embodiment, the activity of the mutated lpdA gene contained in the *E. coli* of the invention is enhanced.

In one embodiment, the *E. coli* of the invention contains a mutated lpdA gene, and said mutated lpdA gene is in a plasmid or integrated into a chromosome.

In one embodiment, the *E. coli* of the invention further comprises the modifications of inhibited expression of the gene(s) involved in phosphoenolpyruvate:sugar phosphotransferase system (PTS), and/or inhibited activities of the protein(s) encoded by the gene(s) involved in phosphoenolpyruvate:sugar phosphotransferase system (PTS); inhibited expression of pflB and/or adhE gene, and/or inhibited activities of the protein(s) encoded by pflB and/or adhE gene; inhibited expression of ldhA gene, and/or inhibited activity of the protein encoded by ldhA gene; enhanced expression of galP gene and/or exogenous glf gene, and/or enhanced activities of the protein(s) encoded by galP gene and/or exogenous glf gene; and enhanced expression of pck gene, and/or enhanced activity of the protein encoded by pck gene.

In one embodiment, the *E. coli* of the invention comprises inhibited expression of the gene(s) involved in phosphoenolpyruvate:sugar phosphotransferase system (PTS), and/or inhibited activities of the protein(s) encoded by the gene(s) involved in phosphoenolpyruvate:sugar phosphotransferase system (PTS), wherein said genes are one or more genes selected from the group consisting of genes ptsI encoding PTS system enzyme I, ptsH encoding PTS system enzyme Hpr, crr encoding PTS system enzyme $IIA^{Glc}$, and ptsG encoding PTS system enzyme $IICB^{Glc}$.

In one embodiment, the *E. coli* of the invention further comprises the modifications of inhibited expression of pflB gene, and/or inhibited activity of the protein encoded by pflB gene; inhibited expression of ldhA gene, and/or inhibited activity of the protein encoded by ldhA gene; and inhibited expression of frdABCD gene cluster, and/or inhibited activities of the protein(s) encoded by frdABCD gene cluster.

In one embodiment, the *E. coli* of the invention further comprises the modifications of enhanced expression of aceEF gene cluster, and/or enhanced activities of the protein(s) encoded by aceEF gene cluster.

In second aspect, the invention provides a method for producing chemical material, comprising a step of culturing the *E. coli* of the invention.

In one embodiment, the invention provides a method for producing ethanol, succinate, butanol, and/or 1,3-propanediol, comprising a step of culturing the *E. coli* of the invention.

In third aspect, the invention relates to use of the *E. coli* of the invention in the production of chemical material.

In one embodiment, the invention relates to use of the *E. coli* of the invention in the production of ethanol, succinate, butanol, and/or 1,3-propanediol.

BRIEF DESCRIPTION OF FIGURES

FIG. 4: (A) Nucleotide sequence alignment of the wild-type lpdA gene and mutated lpdA gene (lpdA*); (B) Amino acid sequence alignment of the polypeptides encoded by the wild-type lpdA gene and mutated lpdA gene (lpdA*).

DETAILED DESCRIPTION OF THE INVENTION

Figure 1:
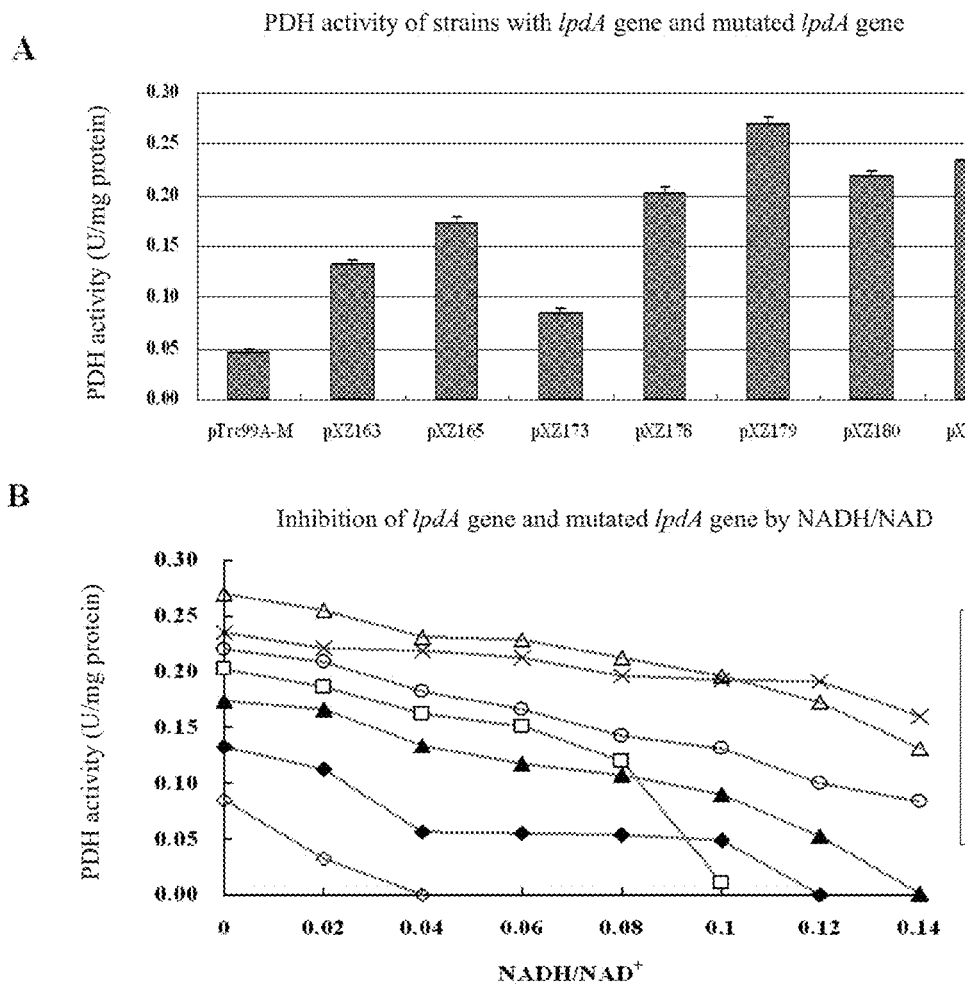
FIG. 1: (A) PDH activity of strains with wild-type lpdA gene and mutated lpdA gene; (B) Inhibition of lpdA gene and mutated lpdA gene by NADH/NAD.

Unless otherwise indicated, all technical and scientific terms have the common meanings known in the art. All the patents, patent applications, publications, sequences, and other published material are incorporated herein as references, unless otherwise indicated.

In one aspect, the invention provides a recombinant *E. coli* comprising a mutated lpdA gene.

As used herein, the term "engineered recombinant *E. coli*", "engineered *E. coli*" and "recombinant *E. coli*" can be used interchangeably, and refer to a genetically modified *E. coli*, wherein the genetic modification can be, e.g., enhanced gene expression, inhibited gene expression, introduction of a new gene, introduction of a mutated gene, or mutating a gene; wherein common techniques in the art can be used to achieve enhanced gene expression or inhibited gene expression, such as deleting a gene, altering gene copy number, introducing a plasmid, changing a gene promoter (e.g. using a strong promoter or a weak promoter) etc.

In one embodiment, the invention provides a recombinant *E. coli* comprising a mutated lpdA gene, wherein the polypeptide encoded by the mutated lpdA gene comprises modification(s) at one or more positions corresponding to the positions T81, P275, and A358 of the amino acid sequence shown in SEQ ID No.: 1, wherein the corresponding positions are determined by aligning the sequence of the polypeptide with SEQ ID No.: 1. In one preferred embodiment, in the *E. coli*, the expression of said mutated lpdA gene is enhanced, and/or the activity of the protein encoded by said mutated lpdA gene is enhanced.

In one embodiment, the invention provides a recombinant *E. coli* comprising a mutated lpdA gene, wherein the polypeptide encoded by the mutated lpdA gene comprises modification(s) at one or more positions corresponding to the positions T81, P275, and A358 of the amino acid sequence shown in SEQ ID No.: 1, wherein the corresponding positions are determined by aligning the sequence of the polypeptide with SEQ ID No.: 1, and wherein at the position corresponding to T81, T is replaced with I, at the position corresponding to P275, P is replaced with S, and at the position corresponding to A358, A is replaced with V. In one preferred embodiment, in the E. coli, the expression of said mutated lpdA gene is enhanced, and/or the activity of the protein encoded by said mutated lpdA gene is enhanced.

The term "mutation" has the common meanings known in the art, and refers to insertion, addition, deletion, or replacement of one or more nucleotides in a nucleotide sequence, or insertion, addition, deletion, or replacement of one or more amino acids in a polypeptide sequence.

In one embodiment, the invention provides an E. coli comprising a mutated lpdA gene, wherein said mutated lpdA gene comprises modifications at one or more positions corresponding to the positions C242, C823, and C1073 of the nucleotide sequence shown in SEQ ID No.: 2, wherein the corresponding positions are determined by aligning the sequence of the gene with SEQ ID No.: 2. In one preferred embodiment, in the E. coli, the expression of said mutated lpdA gene is enhanced, and/or the activity of the protein encoded by said mutated lpdA gene is enhanced.

In one embodiment, the invention provides an E. coli comprising a mutated lpdA gene, wherein said mutated lpdA gene comprises modifications at one or more positions corresponding to the positions C242, C823, and C1073 of the nucleotide sequence shown in SEQ ID No.: 2, wherein the corresponding positions are determined by aligning the sequence of the gene with SEQ ID No.: 2, and wherein said mutations all are the replacement of C with T. In one preferred embodiment, in the E. coli, the expression of said mutated lpdA gene is enhanced, and/or the activity of the protein encoded by said mutated lpdA gene is enhanced.

lpdA gene (Genbank No: ACA79157.1) is a gene encoding lipoamide dehydrogenase (EC No: 1.8.1.4). In one embodiment of the invention, in the starting E. coli strain, the nucleotide sequence of the wild-type lpdA gene is set forth in SEQ ID No.: 2, and the amino acid sequence of the polypeptide encoded by it is set forth in SEQ ID No.: 1. In one embodiment, the mutated lpdA gene contained in the E. coli of the invention comprises one or more of the mutations C242T, C823T, and C1073T (see FIG. 4A); and the polypeptide encoded by said mutated lpdA gene has one or more of the amino acid replacements T81I, P275S, and A358V (see FIG. 4B).

A person skilled in the art will understand that, the sequences of lpdA genes of different E. coli strains might be not completely identical to the lpdA gene sequence as shown in SEQ ID No.: 2, and the polypeptide sequences encoded by lpdA genes from different E. coli strains might be not completely identical to the polypeptide sequence as shown in SEQ ID No.: 1. In some embodiments of the invention, said mutations in the mutated lpdA gene are at positions C242, 823, and/or 1073 of SEQ ID No.: 2. In some embodiments of the invention, the replacements in the polypeptide encoded by the mutated lpdA gene are at positions corresponding to positions 81, 275, and/or 358 of SEQ ID No.: 1.

In the invention, "corresponding to" one specific position in SEQ ID No.: 1 or SEQ ID No.: 2 can be determined by sequence alignment, comprising using manual alignment, and using various available alignment programs (e.g. BLASTP), as well as other means known by a person skilled in the art. By aligning the polypeptide or nucleotide sequences, a person skilled in the art can introduce a corresponding mutation at a proper position, so as to achieve the technical effects of the invention. Besides, a person skilled in the art can also use a conserved or similar amino acid residue to replace the amino acid residue at a corresponding position, or introduce a synonymous mutation into the lpdA gene sequence, so as to achieve the technical effects of the invention.

In one embodiment, the invention provides an E. coli comprising a mutated lpdA gene, wherein the polypeptide encoded by said mutated lpdA gene comprises a modification at the position corresponding to position A358 of the amino acid sequence shown in SEQ ID No.: 1. In one preferred embodiment, the invention provides an E. coli comprising a mutated lpdA gene, wherein the polypeptide encoded by said mutated lpdA gene comprises a modification at the position corresponding to position A358 of the amino acid sequence shown in SEQ ID No.: 1, and the modification at the position corresponding to A358 is the replacement of A with V.

In one embodiment, the invention provides an E. coli comprising a mutated lpdA gene, wherein the mutated lpdA gene comprises a modification at the position corresponding to position C1073 of the nucleotide sequence shown in SEQ ID No.: 2. In one preferred embodiment, the invention provides an E. coli comprising a mutated lpdA gene, wherein the mutated lpdA gene comprises a modification at the position corresponding to position C1073 of the nucleotide sequence shown in SEQ ID No.: 2, and wherein said mutation is the replacement of C with T.

In one embodiment, the invention provides an E. coli comprising a mutated lpdA gene, wherein the polypeptide encoded by said mutated lpdA gene comprises modifications at the positions corresponding to positions T81, P275, and A358 of the amino acid sequence shown in SEQ ID No.: 1. In one preferred embodiment, the invention provides an E. coli comprising a mutated lpdA gene, wherein the polypeptide encoded by said mutated lpdA gene comprises modifications at the positions corresponding to positions T81, P275, and A358 of the amino acid sequence shown in SEQ ID No.: 1, and wherein at the position corresponding to T81, T is replaced with I, at the position corresponding to P275, P is replaced with S, and at the position corresponding to A358, A is replaced with V.

In one embodiment, the invention provides an E. coli comprising a mutated lpdA gene, wherein said mutated lpdA gene comprises mutations at the positions corresponding to positions C242, C823, and C1073 of the nucleotide sequence shown in SEQ ID No.: 2. In one preferred embodiment, the invention provides an E. coli comprising a mutated lpdA gene, wherein said mutated lpdA gene comprises mutations at the positions corresponding to positions C242, C823, and C1073 of the nucleotide sequence shown in SEQ ID No.: 2, and wherein said mutations all are the replacement of C with T.

In one preferred embodiment, in the E. coli, the expression of said mutated lpdA gene is enhanced, and/or the activity of the protein encoded by said mutated lpdA gene is enhanced.

As used herein, the term "enhanced expression of a gene" has the common meanings known in the art, and refers to enhanced intensity of the gene expression, which results in increased amount of mRNAs generated from the gene transcription. The enhanced expression of a gene can be achieved by the ways of, for example, but not limited to: introducing a strong promoter before a gene, increasing the copy number of a gene, or enhancing the stability of mRNA etc. As used herein, the term "enhanced activity of a protein encoded by a gene" has the common meanings known in the art, and refers to the increase of the activity of the protein after the gene transcription and translation, which can be achieved by e.g. enhancing the intensity of the gene expression, increasing the content of an enzyme in a cell, and introducing a mutation at an amino acid site. Various technical means used to achieve the "enhanced expression of a gene" and "enhanced activity of a protein encoded by a gene" are well known for a person skilled in the art.

In the present invention, the enhanced expression of a gene can be achieved by e.g. introducing a strong promoter. In some embodiments of the invention, the strong promoter used can be e.g.: Ppck* (SEQ ID No.: 5) (Zhang et al., 2009b, Appl Environ Microbiol 75:7807-7813) or M1-93 (SEQ ID No.: 6) (Lu et al., 2012, Appl Microbiol Biotechnol 93: 2455-2426).

In one embodiment, the E. coli of the invention comprises a mutated lpdA gene, and said mutated lpdA gene is in a plasmid or a chromosome.

In one embodiment, the E. coli of the invention comprises a mutated lpdA gene, and said mutated lpdA gene is in a chromosome.

In one embodiment, the E. coli of the invention comprises a mutated lpdA gene, and said mutated lpdA gene is in a plasmid.

As used herein, the term "plasmid" has a definition well known in the art, which refers to a DNA molecule that is a non-chromosome DNA existing in a cell in episome form, and capable of self-replicating. Plasmids that can be used in the invention can be e.g.: pEASY-Blunt, pACYC184, pTrc99A, pTrc99A-M, pTrc99A-M-Kan, pKD4, and pKD46 etc.

As used herein, the term "chromosome" has a definition well known in the art. In some embodiments, the modified gene according to the invention is in a chromosome. Techniques that integrate a modified gene into a chromosome are well known to a person skilled in the art, e.g. see Michael R. Green and Joseph Sambrook, "Molecular Cloning: A Laboratory Manual" (Fourth Edition).

In one embodiment, the E. coli of the invention further comprises one or more of the modifications of inhibited expression of the gene(s) involved in phosphoenolpyruvate:sugar phosphotransferase system (PTS), and/or inhibited activities of the protein(s) encoded by the gene(s) involved in phosphoenolpyruvate:sugar phosphotransferase system (PTS); inhibited expression of pflB and/or adhE genes, and/or inhibited activities of the protein(s) encoded by pflB and/or adhE genes; inhibited expression of ldhA gene, and/or inhibited activity of the protein encoded by ldhA gene; enhanced expression of galP gene and/or exogenous glf gene, and/or enhanced activities of the protein(s) encoded by galP gene and/or exogenous glf gene; and enhanced expression of pck gene, and/or enhanced activity of the protein encoded by pck gene.

In one embodiment, the E. coli of the invention comprises inhibited expression of the gene(s) involved in phosphoenolpyruvate:sugar phosphotransferase system (PTS), and/or inhibited activities of the protein(s) encoded by the gene(s) involved in phosphoenolpyruvate:sugar phosphotransferase system (PTS), wherein said gene(s) are one or more genes selected from the group consisting of genes ptsI encoding PTS system enzyme I, ptsH encoding PTS system enzyme Hpr, crr encoding PTS system enzyme IIA$^{Glc}$ and ptsG encoding PTS system enzyme IICB$^{Glc}$.

In the invention, ptsI gene (GenBank No: ACA76928.1, NC_010468.1) encodes a phosphotransferase, also called phosphoenolpyruvate sugar phosphotransferase enzyme I (EC No: 2.7.3.9), ptsH gene (GenBank No: ACA76929.1) encodes phosphoenolpyruvate sugar phosphotransferase enzyme Hpr (EC No: 2.7.1.69), crr gene (GenBank No: ACA76927.1) encodes phosphoenolpyruvate sugar phosphotransferase enzyme IIA$^{Glc}$ (EC No: 2.7.1.69), and ptsG gene (GenBank No: ACA78131.1) encodes phosphoenolpyruvate sugar phosphotransferase enzyme IICB$^{Glc}$ (EC No: 2.7.1.69).

In one embodiment, the E. coli of the invention further comprises one or more of the modifications of inhibited expression of ptsI gene, and/or inhibited activity of the protein encoded by ptsI gene; inhibited expression of pflB and/or adhE genes, and/or inhibited activities of the protein(s) encoded by pflB and/or adhE genes; inhibited expression of ldhA gene, and/or inhibited activity of the protein encoded by ldhA gene; enhanced expression of galP gene and/or exogenous glf gene, and/or enhanced activities of the protein(s) encoded by galP gene and/or exogenous glf gene; and enhanced expression of pck gene, and/or enhanced activity of the protein encoded by pck gene.

In one embodiment, the E. coli of the invention further comprises one or more of the modifications of inhibited expression of ptsI gene, and/or inhibited activity of the protein encoded by ptsI gene; inhibited expression of pflB and/or adhE genes, and/or inhibited activities of the protein(s) encoded by pflB and/or adhE genes; inhibited expression of ldhA gene, and/or inhibited activity of the protein encoded by ldhA gene; enhanced expression of galP gene, and/or enhanced activity of the protein encoded by galP gene; and enhanced expression of pck gene, and/or enhanced activity of the protein encoded by pck gene.

In one embodiment, the E. coli of the invention further comprises one or more of the modifications of inhibited expression of ptsI gene, and/or inhibited activity of the protein encoded by ptsI gene; inhibited expression of pflB gene, and/or inhibited activity of the protein encoded by pflB gene; inhibited expression of ldhA gene, and/or inhibited activity of the protein encoded by ldhA gene; enhanced expression of galP gene, and/or enhanced activity of the protein encoded by galP gene; and enhanced expression of pck gene, and/or enhanced activity of the protein encoded by pck gene.

In one embodiment, the E. coli of the invention further comprises a modification selected from the group consisting of inhibited expression of ptsI gene, and/or inhibited activity of the protein encoded by ptsI gene; inhibited expression of pflB gene, and/or inhibited activity of the protein encoded by pflB gene; inhibited expression of ldhA gene, and/or inhibited activity of the protein encoded by ldhA gene; enhanced expression of galP gene, and/or enhanced activity of the protein encoded by galP gene; and enhanced expression of pck gene, and/or enhanced activity of the protein encoded by pck gene.

In the invention, pflB gene (GenBank No: ACA78322.1) encodes pyruvate formate lyase (EC No. 2.3.1.54), adhE gene (Genbank No: ACA78022.1) encodes ethanol/acetaldehyde dehydrogenase (EC No: 1.1.1.1, EC No: 1.2.1.10), ldhA gene (GenBank No: ACA77176.1) encodes lactate dehydrogenase A (EC No: 1.1.1.28), galP gene (GenBank No: ACA76443.1) encodes galactose MFS transporter, glf gene (GenBank No: AAA27691.1) encodes glucose transporter Glf (glucose facilitator protein), and pck gene (GenBank No: ACA75988.1) encodes phosphoenolpyruvate carboxykinase, also called PCK enzyme (EC No: 4.1.1.49).

As used herein, the term "inhibited expression of a gene" has the common meanings known in the art, and refers to the decreased intensity of the expression of a gene, resulting in the decreased amount of mRNAs generated from gene transcription. The inhibited expression of a gene can be achieved by the ways of, for example but not limited to: deleting a gene, decreasing gene copy number, altering gene promoter (e.g. using a weak promoter) etc. As used herein, the term "inhibited activity of a protein encoded by a gene" has the common meanings known in the art, and refers to the decreased activity of a protein encoded by a gene. It can be achieved by, e.g. decreasing the intensity of the expression of a gene, inserting or deleting a nucleotide in a gene, or mutating at an amino acid site. Various technical means for achieving the "inhibited expression of a gene" and "inhibited activity of a protein encoded by a gene" are well known for a person skilled in the art.

In one embodiment, the *E. coli* of the invention further comprises the modifications of inhibited expression of frdABCD gene cluster, and/or inhibited activities of the protein(s) encoded by frdABCD gene cluster.

The frdABCD gene cluster encodes fumarate reductase (EC No: 1.3.5.4), including frdA gene (GenBank No: ACA79460.1) encoding fumarate reductase flavoprotein subunit, frdB gene (GenBank No: ACA79461.1) encoding fumarate reductase iron-sulphur protein subunit, frdC gene (GenBank No: ACA79462.1) encoding fumarate reductase subunit C, and frdD gene (GenBank No: ACA79463.1) encoding fumarate reductase subunit D.

In one embodiment, the *E. coli* of the invention further comprises one or more of the modifications of inhibited expression of pflB gene, and/or inhibited activity of the protein encoded by pflB gene; inhibited expression of ldhA gene, and/or inhibited activity of the protein encoded by ldhA gene; and inhibited expression of frdABCD gene cluster, and/or inhibited activities of the protein(s) encoded by frdABCD gene cluster.

In another embodiment, the *E. coli* of the invention further comprises the modifications of inhibited expression of pflB gene, and/or inhibited activity of the protein encoded by pflB gene; inhibited expression of ldhA gene, and/or inhibited activity of the protein encoded by ldhA gene; and inhibited expression of frdABCD gene cluster, and/or inhibited activities of the protein(s) encoded by frdABCD gene cluster.

In one embodiment, the *E. coli* of the invention further comprises the modification(s) of enhanced expression of aceEF gene cluster, and/or enhanced activities of the protein(s) encoded by aceEF gene cluster.

The aceEF gene cluster encode pyruvate complex E1/E2, including aceE gene (GenBank No: ACA79159.1) encoding pyruvate dehydrogenase complex E1 and aceF gene (GenBank No: ACA79158.1) encoding pyruvate dehydrogenase complex E2.

In the invention, an enhancing method includes RBS library regulation: a strategy of increasing the expression level of a gene by using ribosome binding site (RBS) library sequences (nucleotides are composed of random bases).

In second aspect, the invention provides a method for producing a chemical material, comprising a step of culturing the *E. coli* of the invention.

In one embodiment, the method of the invention comprises culturing the *E. coli* of the invention, and optionally collecting or purifying the obtained chemical material.

The method of the invention can be used to produce various chemical materials that could be produced by microbial fermentation, including but not limited to: succinate, ethanol, butanol, and 1,3-propanediol etc.

In one embodiment, the "culturing" of the invention includes seed culture and fermentation culture.

As used herein, the term "seed culture" refers to a process that, after activating a bacterial strain stock for fermentation on a solid medium, the activated bacteria are then scaled up in shaking flask and seed tank, so as to obtain a certain amount and quality of pure seed.

As used herein, the term "fermentation culture" refers to a process that, by using a microbe species, and under proper conditions, the components of a medium are converted into some specific products through particular metabolic pathway(s).

In one embodiment, the method of the invention comprises performing anaerobic fermentation of the *E. coli* of the invention.

As used herein, the term "anaerobic fermentation" refers to a process that, by using an anaerobic fermentation bacterial strain, and under anoxic conditions, the components of a medium are converted into some specific products through particular metabolic pathway(s).

In one embodiment, the culture process in the method of the invention does not involve any aeration step.

In one embodiment, the method of the invention of culturing *E. coli* comprises the steps of:

(1) inoculating the recombinant *E. coli* of the invention into a seed medium, and culturing under a condition suitable for *E. coli* growth for a period to obtain a seed solution;

(2) inoculating the seed solution into a fermentation medium, and culturing under an anaerobic condition.

In the method of the invention, various conventional culturing conditions for *E. coli* can be used, such as medium, culture temperature, culture period, and whether using a shaker as well as the shaking speed etc. A person skilled in the art can choose proper conditions based on the requirements. The culturing conditions and the fermentation conditions used in the method of the invention are well known for a person skilled in the art (Zhuge Jian et al., 1994, *Industrial Microbiology Experimental Techniques Manual*, China Light Industry Press).

In one embodiment, the culture condition of the invention includes but not limited to a temperature of 30-45° C., e.g. 30-31° C., 31-32° C., 32-33° C., 33-34° C., 34-35° C., 35-36° C., 36-37° C., 37-38° C., 38-39° C., 39-40° C., 40-41° C., 41-42° C., 42-43° C., 43-44° C., or 44-45° C.

In one embodiment, the culture condition of the invention includes but not limited to a seed culture period of 6-16 hours, e.g. 6-7 hours, 7-8 hours, 8-9 hours, 9-10 hours, 10-11 hours, 11-12 hours, 12-13 hours, 13-14 hours, 14-15 hours, or 15-16 hours.

In one embodiment, the culture condition of the invention includes but not limited to: a fermentation culture period of 2-5 days, e.g. 2 days, 3 days, 4 days, or 5 days.

In one embodiment, the culture condition of the invention includes but not limited to, inoculating the recombinant *E. coli* of the invention into a seed medium at an inoculation amount of 0.1-10% (V/V), e.g. 0.1%, 0.5%, 1%, 2.5%, 5%, or 10%.

In one embodiment, the culture condition of the invention includes but not limited to, inoculating the seed solution into a fermentation medium at an inoculation amount of a final concentration of $OD_{550}$=0.05-0.5, e.g. 0.05-0.1, 0.1-0.2, 0.2-0.3, 0.3-0.4, or 0.4-0.5.

In one embodiment, the medium commonly used for *E. coli* can be used. The medium used for the *E. coli* of the invention can comprise a proper nitrogen source, e.g. organic nitrogen compounds, or inorganic nitrogen compounds, or mixtures thereof. In one embodiment, said organic nitrogen compound can be e.g. selected from one or a mixture of the following: soybean meal, peanut meal, beef extract, fish meal, yeast extract, peptone, corn steep liquor; said inorganic nitrogen compound can be e.g. selected from one or a mixture of the following: nitrate salts (such as sodium nitrate, potassium nitrate, calcium nitrate), ammonium salts (such as ammonium phosphate, ammonium sulfate, ammonium nitrate, ammonium chloride). In one embodiment, the medium used for the *E. coli* of the invention can comprise a proper carbon source, e.g. selected from one or a mixture of the following: glucose, starch, saccharine generated from amylohydrolysis, fructose, dextrin, lactose, galactose, xylose, sucrose, glycerol, maltose, fatty acid, acetate, pyruvate, and fumarate.

In one embodiment, the seed medium and the fermentation medium used in the method of the invention are composed of (using water as solvent):

Major elements: glucose, $KH_2PO_4$, $K_2HPO_4$, $(NH_4)_2HPO_4$, $MgSO_4.7H_2O$, and betaine-KCl; and Trace elements: $FeCl_3.6H_2O$, $CoCl_2.6H_2O$, $CuCl_2.2H_2O$, $ZnCl_2$, $Na_2MoO_4.2H_2O$, $MnCl_2.4H_2O_2$, and $H_3BO_3$.

In one embodiment, the medium of the invention is composed of (using water as solvent):

Major elements: glucose 20-120 g/L, $KH_2PO_4$ 2-5 g/L, $K_2HPO_4$ 4-8 g/L, $(NH_4)_2HPO_4$ 3-5 g/L, $MgSO_4.7H_2O$ 0.1-0.3 g/L, and betaine-KCl 0.1-1 g/L; and Trace elements: $FeCl_3.6H_2O$ 1-5 μg/L, $CoCl_2.6H_2O$ 0.05-1 μg/L, $CuCl_2.2H_2O$ 0.05-1 μg/L, $ZnCl_2$ 0.05-1 μg/L, $Na_2MoO_4.2H_2O$ 0.05-1 μg/L, $MnCl_2.4H_2O_2$ 0.1-1 μg/L, $H_3BO_3$ 0.01-0.5 μg/L.

In one embodiment, the method of the invention for culturing *E. coli* is specifically as following:

Anaerobic fermentation of the bacterial strain, comprising the following steps:

(1) Seed culture: placing ⅓-½ volume of seed medium in a triangular flask, and autoclaving for sterilization. After cooling down, inoculating the recombinant *E. coli* of the invention at an inoculation amount of 0.1-10% (V/V) into a seed medium, and culturing at 37° C. for 6-16 hours under shaking conditions to obtain a seed solution for inoculating a fermentation medium;

(2) Fermentation culture: placing ⅓-½ volume of fermentation medium in an anaerobic fermentation vessel, inoculating the seed solution into the fermentation medium at an inoculation amount of a final concentration of $OD_{550}$=0.05-0.5, and culturing at 37° C. for 2-5 days, to obtain fermentation broth.

In one embodiment, the method of the invention for producing chemical material further comprises a step of collecting, extracting, isolating and/or purifying the obtained chemical material.

In third aspect, the invention relates to use of the *E. coli* of the invention in the production of succinate.

EXAMPLES

The invention is further illustrated through the following examples, but any example or combination thereof should not be construed as limiting the scope or embodiment of the invention. The scope of the invention is defined by the attached claims, and based on the present specification and common knowledge in the art, a person skilled in the art can clearly understand the scope as defined by the claims. As long as the spirit and scope of the invention is obeyed, a person skilled in the art can make any modifications or changes to the technical solutions of the invention, and such modifications or changes are also included into the scope of the invention.

The experimental processes used in the following examples are all conventional processes, unless otherwise indicated. The material, reagents etc. used in the following examples are all commercially available, unless otherwise indicated.

Example 1

Construction of Strain HX024

*E. coli* ATCC 8739 was metabolically engineered for succinate production through deleting lactate dehydrogenase gene ldhA, pyruvate formate lyase gene pflB and phosphoenolpyruvate sugar phosphotransferase enzyme I gene ptsI, activating galactose MFS transporter GalP and phosphoenolpyruvate carboxykinase PCK, deleting phosphotransacetylase gene pta and acetate kinase gene ackA, and activating malate synthase AceA, isocitrate lyase AceB and dicarboxylate transporter protein DcuC, resulting in strain NZ-037.

After metabolic evolution of NZ-037 for 1080 generations, the strain HX021 was obtained.

The mgsA gene (GenBank No. ACA78263.1) was deleted from strain HX021 to obtain the recombinant *E. coli* HX023.

After metabolic evolution of HX023 for 360 generations, the strain HX024 was obtained. The recombinant strain HX024 was deposited at CGMCC (Institute of Microbiology of Chinese Academy of Sciences, NO. 1 Beichen West Road, Chaoyang District, Beijing) on Feb. 25, 2013 under the depositary No. of CGMCC 7259. The details for construction of HX024 was described in the invention "Recombinant *E. coli* for Producing Succinate and Use Thereof", which was filed by the same applicant on the same date.

Example 2

Cloning lpdA Gene and Mutated lpdA Gene into pTrc99A-M (1) Construction of the plasmids pXZ163 and pXZ174 (containing lpdA gene from *E. coli* ATCC 8739 (Gunsalus et al., 1941, J Biol Chem 141:853-858) and the strain HX024 (CGMCC 7259), respectively).

Taking the genomic DNA of *E. coli* ATCC 8739 and HX024 as template, amplification products were amplified using a primer set 8739-lpdA-up-SacI/8739-lpdA-down-PstI (SEQ ID No.: 7/SEQ ID No.: 8). The resulting PCR products were digested with SacI and PstI (NEB, UK) at 37° C. for 30 min, and the plasmid pTrc99A-M was digested with the same enzymes (Shi et al., 2013, Metab Eng 16:1-10). The digested products were cleaned using Purification Kit Cleaning Gel/PCR Extraction kit (BioMIGA Biotechnology Company). Cloning system: 50 ng of the fragment of interest and 20 ng of pTrc99A-M fragment were added with 2 μl of 10XT4 ligase buffer solution (NEB), 1 μl of T4 polynucleotide kinase (NEB), supplemented with distilled water to 20 μl of total volume, and reacted at 37° C. for 30 minutes; 1 μl of T4-DNA ligase (NEB, 400,000 cohesive end units/ml) was added and reacted at room temperature for 2 hours to obtain ligation product. The transformation of $CaCl_2$-competent cells: adding 5 μl of the ligation product to the tube containing 50 μl of Trans1-T1 Competent Cells (Beijing TransGen Biotech), and storing it on ice for 30 minutes; 42° C. for heat shock 30 seconds, immediately transferring the tube on ice for 2 minutes; adding 250 μl of LB medium and incubated the culture at 37° C. for 1 hour (200 rpm). 200 μl of transformed competent cells were plated onto a LB plate containing kanamycin (final concentration of 50 μg/mL), and grown for overnight. 5 positive colonies were picked and validated by colony PCR using a primer set pTrc99A-F/pTrc99A-R (SEQ ID No.: 17/SEQ ID No.: 18). The plasmid from corrected colony was sequenced, and the positive one was designated as pXZ163 or pXZ174 (Table 3).

(2) Construction of the plasmids pXZ165 (mutated lpdA encoding one changed amino acid E354A), pXZ173 (mutated lpdA encoding one changed amino acid T81I), pXZ178 (mutated lpdA encoding one changed amino acid P275S) and pXZ179 (mutated lpdA encoding one changed amino acid A358V)

Taking DNA of plasmid pXZ163 as template, an inside-out PCR was employed using primer sets of 8739-lpdA-E354K-F/8739-lpdA-E354K-R (SEQ ID No.: 9/SEQ ID No.: 10), 8739-lpdA-T81I-F/8739-lpdA-T81I-R (SEQ ID No.: 11/SEQ ID No.: 12), 8739-lpdA-P275S-F/8739-lpdA-P275S-R (SEQ ID No.: 13/SEQ ID No.: 14) and 8739-lpdA-A358V-F/8739-lpdA-A358V-R (SEQ ID No.: 15/SEQ ID No.: 16), respectively. The obtained fragments of about 4 kb were digested with restriction enzyme DpnI (NEB) at 37° C. for 30 min, and cleaned using PCR Purification Kit (Gel/PCR Extraction kit, BioMIGA Biotechnology Company, Limited). Cloning system: 30 ng of purified PCR amplification products was added with 2 μl of 10XT4 ligation buffer (NEB) and 1 μl of T4-polynucleotide kinase (NEB), added with distilled water to a volume of 20 μl, reacted at 37° C. for 30 min, and then added with 1 μl of T4 ligase (NEB, 400,000 cohesive end units/ml), at room temperature for 2 hours to obtain ligation products. CaCl₂ transformation was the same as that of the section (1) of Example 2. 200 μl of transformed competent cells were plated on a LB plate containing ampicillin (final concentration of 50 μg/mL), and incubated overnight. Plasmids from 2-3 colonies were sequenced, and the correct ones were designated as pXZ165, pXZ173, pXZ178 and pXZ179, respectively (Table 3).

(3) Construction of the plasmid pXZ180 (mutated lpdA encoding two changed amino acid P275S and A358V)

Taking DNA of plasmid pXZ178 (mutated lpdA encoding one changed amino acid P275S) as template, an inside-out PCR was performed by using a primer set 8739-lpdA-A358V-F/8739-lpdA-A358V-R (SEQ ID No.: 15/SEQ ID No.: 16). The obtained fragments of about 4 kb were digested with restriction enzyme DpnI (NEB) at 37° C. for 30 min, and cleaned by using PCR Purification Kit (Gel/PCR Extraction kit, BioMIGA Biotechnology Company, Limited). Cloning system was the same as that of the section (2) of Example 2. The CaCl₂ transformation was the same to the section (1) of Example 2. 250 μl of LB medium was added, and at 37° C. 200 rpm for 1 hour. 200 μl of transformed competent cells were plated on a LB plate containing ampicillin (final concentration of 50 μg/mL), and incubated overnight. Plasmids from 2-3 clones were sequenced, and the correct one was designated as pXZ180 (Table 3).

TABLE 1

Strains constructed in the invention

| Strain | Characteristic$^a$ |
|---|---|
| ATCC 8739 | Wild-type E. coli |
| Suc-T102 | ATCC 8739, ΔldhA |
| Suc-T104 | ATCC 8739, ΔldhA, ΔpflB |
| ET-T006 | ATCC 8739, ΔldhA, ΔpflB, Δfrd |
| JC-007 | ET-T006, ackA::FRT-Km-lpdA* |
| JC-009 | ET-T006, ackA::M1-93-lpdA* |
| JC-015 | ET-T006, ackA::RBSL10-lpdA* |
| JC-018 | ET-T006, ackA::RBSL10-lpdA*, RBSL1-aceEF |
| JC-019 | ET-T006, RBSL1-aceEF |
| Suc-T106 | ATCC 8739, ΔldhA, ΔpflB, ΔptsI |
| Suc-T108 | ATCC 8739, ΔldhA, ΔpflB, ΔptsI, Ppck*-galP |
| Suc-T110 | ATCC 8739, ΔptsI, ΔldhA, ΔpflB, Ppck*-galP, Ppck*-pck |
| NZ-035 | Suc-T110, ΔackA-pta |
| NZ-038 | Suc-T110, ackA::M1-93-lpdA* |
| NZ-041 | Suc-T110, M1-93-aceEF, ackA::M1-93-lpdA* |
| NZ-098 | Suc-T110, RBSL1-aceEF |
| NZ-099 | Suc-T110, ackA::RBSL10-lpdA* |
| NZ-100 | Suc-T110, RBSL1-aceEF, ackA::RBSL10-lpdA* |

Ppck* (SEQ ID No.: 5) represented mutated pck promoter (including G to A transition at position −64 relative to the ATG start codon) (Zhang et al., 2009a). M1-93 (SEQ ID No.: 6) were artificial regulatory parts constructed previously, and their strengths were 5 times of induced E. coli lacZ promoter (Lu et al., 2012). lpdA* represented triple mutated LpdA (T81I, P275S and A358V).

TABLE 2

Primers used in the invention

| Primer name | Sequence |
|---|---|
| | lpdA and mutated lpdA gene cloned |
| 8739-lpdA-up-SacI | GCATGAGCTCAAGGAGATATACCATGAGTACTGAAATCAAAACTC (SEQ ID No: 7) |
| 8739-lpdA-down-PstI | GCATCTGCAGTTACTTCTTCTTCGCTTTCGGGTTC (SEQ ID No: 8) |
| 8739-lpdA-E354K-F | GTTGCATGGGTGGGTCTGAC (SEQ ID No.: 9) |
| 8739-lpdA-E354K-R | TTCTGGTTTGGTATAGGCGATGGACGGGATA (underline: mutated site) (SEQ ID No.: 10) |
| 8739-lpdA-T81I-F | TCGACAAGATTCGTACCTG (SEQ ID No.: 11) |
| 8739-lpdA-T81I-R | TATCGATTTTCGGTTCGCCAAAGACG (underline: mutated site) (SEQ ID No.: 12) |
| 8739-lpdA-P275S-F | GGTAAAAACCTCGACGCAG (SEQ ID No.: 13) |

TABLE 2-continued

Primers used in the invention

| Primer name | Sequence |
|---|---|
| 8739-lpdA-P275S-R | GTTCGACACACGACCAATCGCTAC<br>(underline: mutated site) (SEQ ID No.: 14) |
| 8739-lpdA-A358V-F | GTTGTATGGGTAGGTCTGACTGAG<br>(underline: mutated site) (SEQ ID No.: 15) |
| 8739-lpdA-A358V-R | TTCTGGTTCGGTATAGGC (SEQ ID No.: 16) |
| pTrc99A-F | TTGCGCCGACATCATAAC (SEQ ID No.: 17) |
| pTrc99A-R | CTGCGTTCTGATTTAATCTG (SEQ ID No.: 18) |

Construction of pXZ-CS

| | |
|---|---|
| 184-cat-up | GCTAGGTACCTGTGACGGAAGATCACTTCG (SEQ ID No.: 19) |
| 184-cat-down | GCTAGAGCTCGCGGCTATTTAACGACCCT (SacI) (SEQ ID No.: 20) |
| Bs-sacB-up | GCTAGAGCTCAAGTAAATCGCGCGGGTTT (SacI) (SEQ ID No.: 21) |
| Bs-sacB-down | GCTAGGATCCTTATTTGTTAACTGTTAATTGTC (SEQ ID No.: 22) |
| M13-F | GTAAAACGACGGCCAGT (SEQ ID No.: 23) |
| M13-R | CAGGAAACAGCTATGAC (SEQ ID No.: 24) |

Deletion of ldhA gene

| | |
|---|---|
| XZ-ldhA-up | GATAACGGAGATCGGGAATG (SEQ ID No.: 25) |
| XZ-ldhA-down | CTTTGGCTGTCAGTTCACCA (SEQ ID No.: 26) |
| XZ-ldhA-1 | TCTGGAAAAAGGCGAAACCT (SEQ ID No.: 27) |
| XZ-ldhA-2 | TTTGTGCTATAAACGGCGAGT (SEQ ID No.: 28) |
| cat-sacB-up | TGTGACGGAAGATCACTTCGCA (SEQ ID No.: 29) |
| cat-sacB-down | TTATTTGTTAACTGTTAATTGTCCT (SEQ ID No.: 30) |

Deletion of pflB gene

| | |
|---|---|
| XZ-pflB-up | TGTCCGAGCTTAATGAAAAGTT (SEQ ID No.: 31) |
| XZ-pflB-down | CGAGTAATAACGTCCTGCTGCT (SEQ ID No.: 32) |
| XZ-pflB-1 | AAACGGGTAACACCCCAGAC (SEQ ID No.: 33) |
| XZ-pflB-2 | CGGAGTGTAAACGTCGAACA (SEQ ID No.: 34) |

Deletion of frd gene

| | |
|---|---|
| XZ-frdB-up | TGCAGAAAACCATCGACAAG (SEQ ID No.: 35) |
| XZ-frdC-down | CACCAATCAGCGTGACAACT (SEQ ID No.: 36) |
| XZ-frdC-1 | GCCACCATCGTAATCCTGTT (SEQ ID No.: 37) |
| XZ-frdB-2 | ATAGCGCACCACCTCAATTT (SEQ ID No.: 38) |

Construction of pTrc99A-M-Kan

| | |
|---|---|
| Kan-up-PacI | GCATTTAATTAAGTGTAGGCTGGAGCTGCT (SEQ ID No.: 39) |
| Kan-down-EcoRI | GCATGAATTCCAGAATCGAAATCTC (SEQ ID No.: 40) |
| Kan-F | CCGTGATATTGCTGAAGAG (SEQ ID No.: 41) |

Integration of lpdA* gene

| | |
|---|---|
| ackA-FRT-up | TCATCATGCGCTACGCTCTATGGCTCCCTGACGTTTTTTAGCCAC<br>GTATCAATTATAGGTACTTCCGTGTAGGCTGGAGCTGCTTC<br>(SEQ ID No.: 42) |

TABLE 2-continued

Primers used in the invention

| Primer name | Sequence |
| --- | --- |
| pta-rrnB-down | GTTAAGCAAGATAATCAGAAAGGATTAATGCAGATTAAGAGAATA<br>AAAAACCGGAAATAGTGAAAAAGGCCATCCGTCAGGAT<br>(SEQ ID No.: 43) |
| lpdA-R-170 | AGCAGTGCTTTAGAAGGGATAC (SEQ ID No.: 44) |

Modulation of lpdA* gene

| Primer name | Sequence |
| --- | --- |
| ackA-cat-sacB-up | TCATCATGCGCTACGCTCTATGGCTCCCTGACGTTTTTTTAGCCAC<br>GTATCAATTATAGGTACTTCCTGTGACGGAAGATCACTTCGCA<br>(SEQ ID No.: 45) |
| lpdA-cat-sacB-down | CGGAAGGCAGCGGAGTAACCTGCGGGGCCTGCCCCAAGTACCAC<br>GACCTGAGTTTTGATTTCAGTACTCATCATTTATTTGTTAACTGTTA<br>ATTGTCCT (SEQ ID No.: 46) |
| ackA-P-up | TCATCATGCGCTACGCTCTATGGCTCCCTGACGTTTTTTTAGCCAC<br>GTATCAATTATAGGTACTTCCTTATCTCTGGCGGTGTTGAC<br>(SEQ ID No.: 47) |
| lpdA-RBS-down | CGGAAGGCAGCGGAGTAACCTGCGGGGCCTGCCCCAAGTACCAC<br>GACCTGAGTTTTGATTTCAGTACTCATCATAGCTGTTTCCTGGTT<br>(SEQ ID No.: 48) |

Modulation of lpdA* gene with RBS library

| Primer name | Sequence |
| --- | --- |
| ackA-up-500 | CCAGCCACCACAATCCCT (SEQ ID No.: 49) |
| lpdA-RBSL-down | CGGAAGGCAGCGGAGTAACCTGCGGGGCCTGCCCCAAGTACCAC<br>GACCTGAGTTTTGATTTCAGTACTCATNNNNNNYCTCCTGGT<br>TTAAACGTACATG (SEQ ID No.: 50) |

Modulation of aceEF gene

| Primer name | Sequence |
| --- | --- |
| aceEF-cat-sacB-up | AGACTTCCGTCAGATCAAGAATAATGGTATGCGGCAGCGAATGCA<br>CCCGCTTTATGCATGTGTGACGGAAGATCACTTCGCA<br>(SEQ ID No.: 51) |
| aceEF-cat-sacB-down | CCTGGAGCCAGTCGCGAGTTTCGATCGGATCCACGTCATTTGGGA<br>AACGTTCTGACATTTATTTGTTAACTGTTAATTGTCCT<br>(SEQ ID No.: 52) |
| aceEF-P-up | AGACTTCCGTCAGATCAAGAATAATGGTATGCGGCAGCGAATGCA<br>CCCGCTTTATGCATGTTATCTCTGGCGGTGTTGAC (SEQ ID No.: 53) |
| aceEF-RBS-down | CCTGGAGCCAGTCGCGAGTTTCGATCGGATCCACGTCATTTGGGA<br>AACGTTCTGACATAGCTGTTTCCTG (SEQ ID No.: 54) |
| aceEF-1 | ACGGAAGAAGTGGTTAAAGCACAC (SEQ ID No.: 55) |
| AP1-up | TTATCTCTGGCGGTGTTGAC (SEQ ID No.: 56) |

Modulation of aecEF gene with RBS library

| Primer name | Sequence |
| --- | --- |
| aceEF-FRT-up | AGACTTCCGTCAGATCAAGAATAATGGTATGCGGCAGCGAATGCA<br>CCCGCTTTATGCATGGTGTAGGCTGGAGCTGCTTC (SEQ ID No.: 57) |
| aceEF-RBSL-down | CCTGGAGCCAGTCGCGAGTTTCGATCGGATCCACGTCATTTGGGA<br>AACGTTCTGACATNNNNNNY CTCCTGGTTTAAACGTACATG<br>(SEQ ID No.: 58) |
| aceEF-up-500 | AAGGGCTTGTTGCTTCGT (SEQ ID No.: 59) |

Deletion of ptsI gene

| Primer name | Sequence |
| --- | --- |
| XZ-ptsI-up | CGCATTATGTTCCCGATGAT (SEQ ID No.: 60) |
| XZ-ptsI-down | GCCTTTCAGTTCAACGGTGT (SEQ ID No.: 61) |
| XZ-ptsI-1 | CGGCCCAATTTACTGCTTAG (SEQ ID No.: 62) |
| XZ-ptsI-2 | ATCCCCAGCAACAGAAGTGT (SEQ ID No.: 63) |

TABLE 2-continued

Primers used in the invention

| Primer name | Sequence |
|---|---|
| *Replacing galP promoter with Ppck\** | |
| XZ-galP-P-up | ATCTGCTGCACCCGATCTAC (SEQ ID No.: 64) |
| XZ-galP-P-down | GAACCGGCAACAAACAAAAT (SEQ ID No.: 65) |
| XZ-galP-P-1 | ATGCCTGACGCTAAAAAACAGGG (SEQ ID No.: 66) |
| XZ-galP-P-2 | GATTAAACGCTGTTATCTGCAA (SEQ ID No.: 67) |
| P-pck\*-up-SpeI | GCATACTAGTGTTGGTTATCCAGAATCAAA (SEQ ID No.: 68) |
| P-pck\*-down-KpnI | GCATGGTACCAGCCAATATGTATTGCCTGAATAG (SEQ ID No.: 69) |
| pck\*-F | ACGGTTAACACCCCCAAAAG (SEQ ID No.: 70) |
| pck\*-R | GACAAGGCTCATAGATTTACGTATC (SEQ ID No.: 71) |
| *Replacing pck promoter with Ppck\** | |
| pck-cat-sacB-up | CGCCATATAAACCAAGATTTAACCTTTTGAGAACATTTTCCACACC TAAGTGTGACGGAAGATCACTTCGCA (SEQ ID No.: 72) |
| pck-cat-sacB-down | ATACCATAAGCCTCGAGTTCTTGCGGGGTCAAACCATTGTTAACG CGCATTTATTTGTTAACTGTTAATTGTCCT (SEQ ID No.: 73) |
| pck-YZ-up | ACGCCATAAACAATCCAA (SEQ ID No.: 74) |
| pck-YZ-down | CGCATTTCACTGCTCCTT (SEQ ID No.: 75) |
| *Deletion of ackA-pta gene* | |
| XZ-ackA-up | CGGGACAACGTTCAAAACAT (SEQ ID No.: 76) |
| XZ-pta-down | ATTGCCCATCTTCTTGTTGG (SEQ ID No.: 77) |
| XZ-ackA-2 | AACTACCGCAGTTCAGAACCA (SEQ ID No.: 78) |
| XZ-pta-2 | TCTGAACACCGGTAACACCA (SEQ ID No.: 79) |

TABLE 3

Plasmid constructed in the invention

| | lpdA and mutated lpdA genes cloned |
|---|---|
| pXZ163 | lpdA was amplified by PCR using the genome of *E. coli* ATCC8739 as template (8739-lpdA-up-SacI/8739-lpdA-down-PstI) and cloned into pTrc99A-M vector |
| pXZ165 | the DNA fragment amplified by using the plasmid pXZ163 DNA as template with primers 8739-lpdA-E354K-F/8739-lpdA-E354K-R was phosphorylated and self-ligated (lpdA E354K) |
| pXZ173 | the DNA fragment amplified by using the plasmid pXZ163 DNA as template with primers 8739-lpdA-T81I-F/8739-lpdA-T81I-R was phosphorylated and self-ligated (lpdA T81I) |
| pXZ178 | the DNA fragment amplified by using the plasmid pXZ163 DNA as template with primers 8739-lpdA-P275S-F/8739-lpdA-P275S-R was phosphorylated and self-ligated (lpdA P275S) |
| pXZ179 | the DNA fragment amplified by using the plasmid pXZ163 DNA as template with primers 8739-lpdA-A358V-F/8739-lpdA-A358V-R was phosphorylated and self-ligated (lpdA A358V) |
| pXZ180 | the DNA fragment amplified by using the plasmid pXZ178 DNA as template with primers 8739-lpdA-P275S-F/8739-lpdA-P275S-R was phosphorylated and self-ligated (lpdA P275S A358V) |
| pXZ174 | lpdA was amplified by PCR using the genome of HX-024 as template (8739-lpdA-up-SacI/8739-lpdA-down-PstI) and cloned into pTrc99A-M vector (lpdA\* T81I P275S A358V) |

TABLE 3-continued

| Plasmid constructed in the invention | |
|---|---|
| Deletion of ldhA gene | |
| pXZ001 | ldhA was amplified by PCR using the genome of *E. coli* ATCC8739 as template (XZ-ldhA-up/XZ-ldhA-down) and cloned into pEASY-Blunt vector |
| pXZ002C | cat-sacB cassette was amplified by PCR using pXZ-CS as template (cat-sacB-up/cat-sacB-down) and cloned into the DNA fragment amplified by using the plasmid pXZ001 DNA as template with primers XZ-ldhA-1/XZ-ldhA-2 |
| pXZ003 | the DNA fragment amplified by using the plasmid pXZ001 DNA as template with primers XZ-ldhA-1/XZ-ldhA-2 was phosphorylated and self-ligated |
| Deletion of pflB gene | |
| pXZ014 | pflB was amplified by PCR using the genome of *E. coli* ATCC8739 as template (XZ-pflB-up/XZ-pflB-down) and cloned into pEASY-Blunt vector |
| pXZ015C | cat-sacB cassette was amplified by PCR using pXZ-CS as template (cat-sacB-up/cat-sacB-down) and cloned into the DNA fragment amplified by using the plasmid pXZ014 DNA as template with primers XZ-pflB-1/XZ-pflB-2 |
| pXZ016 | the DNA fragment amplified by using the plasmid pXZ014 DNA as template with primers XZ-pflB-1/XZ-pflB-2 was phosphorylated and self-ligated |
| Deletion of frd gene | |
| pXZ005 | frdABCD was amplified by PCR using the genome of *E. coli* ATCC8739 as template (XZ-frdB-up/XZ-frdC-down) and cloned into pEASY-Blunt vector |
| pXZ006C | cat-sacB cassette was amplified by PCR using pBM002 as template (cat-sacB-up/cat-sacB-down) and cloned into the DNA fragment amplified by using the plasmid pXZ005 DNA as template with primers XZ-frdC-1/XZ-frdB-2 |
| pXZ007 | the DNA fragment amplified by using the plasmid pXZ005 DNA as template with primers XZ-frdC-1/XZ-frdB-2 was phosphorylated and self-ligated |
| **Integration of mutated lpdA (lpdA*)** | |
| pTrc99A-M-Kan | FRT-km fragment amplified by PCR from pKD4 (Kan-up-PacI/Kan-down-EcoRI) was cloned into pTrc99A-M |
| pXZ177 | lpdA* (T81I P275S and A358V) obtained by enzymatically cleaving the plasmid pXZ174 was ligated into pTrc99A-M-Kan |
| Deletion of ackA-pta gene | |
| pXZ023 | ackA-pta was amplified by PCR using the genome of *E. coli* ATCC8739 as template (XZ-ackA-up/XZ-pta-down) and cloned into pEASY-Blunt vector |
| pXZ024C | cat-sacB cassette was amplified by PCR using pXZ-CS as template (cat-sacB-up/cat-sacB-down) and cloned into the DNA fragment amplified by using the plasmid pXZ023 DNA as template with primers XZ-ackA-2/XZ-pta-2 |
| pXZ025 | the DNA fragment amplified by using the plasmid pXZ023 DNA as template with primers XZ-ackA-2/XZ-pta-2 was phosphorylated and self-ligated |
| Deletion of ptsI gene | |
| pXZ008 | ptsI was amplified by PCR using the genome of *E. coli* ATCC8739 as template (XZ-ptsI-up/XZ-ptsI-down) and cloned into pEASY-Blunt vector |
| pXZ009C | cat-sacB cassette was amplified by PCR using pXZ-CS as template (cat-sacB-up/cat-sacB-down) and cloned into the DNA fragment amplified by using the plasmid pXZ008 DNA as template with primers XZ-ptsI-1/XZ-ptsI-2 |
| pXZ010 | the DNA fragment amplified by using the plasmid pXZ008 DNA as template with primers XZ-ptsI-1/XZ-ptsI-2 was phosphorylated and self-ligated |
| Replacing the native promoter of galP gene with Ppck* | |
| pXZ602 | the regulation element pck of phosphoenolpyruvate carboxykinase PCK was amplified by PCR using the genome of *E. coli* ATCC8739 as template (P-pck*-up-SpeI/P-pck*-down-KpnI) and cloned into pTrc99A vector |
| pXZ603 | the DNA fragment amplified by using the plasmid pXZ602 DNA as template with primers pck*-F/pck*-R was phosphorylated and self-ligated |
| pXZ011 | galP was amplified by PCR using the genome of *E. coli* ATCC8739 as template (XZ-galP-P-up/XZ-galP-P-down) and cloned into pEASY-Blunt vector |

TABLE 3-continued

| Plasmid constructed in the invention | |
|---|---|
| pXZ012C | cat-sacB cassette was amplified by PCR using pXZ-CS as template (cat-sacB-up/cat-sacB-down) and cloned into the DNA fragment amplified by using the plasmid pXZ011 DNA as template with primers XZ-galP-P-1/XZ-galP-P-2 |
| pXZ013 | Ppck* promoter (plasmid pXZ603 as template with primers P-pck*-up-SpeI/P-pck*down-KpnI) was cloned into the DNA fragment amplified by using the plasmid pXZ011 DNA as template with primers XZ-galP-P-1/XZ-galP-P-2 |

Example 3

Effect of the Mutated lpdA on PDH Activity and NADH Inhibition

Cell culture and induction: pre-inocula of strains containing one of the above 7 plasmids (pXZ163, pXZ165, pXZ173, pXZ178, pXZ179, pXZ180 or pXZ174) and control plasmid pTrc99A-M (empty plasmid) were grown by transferring fresh colonies into 3 ml of LB medium. After growing overnight, these cultures were diluted into 250 ml flask with 30 ml LB by an inoculum of 1% (v/v), and grown at 37° C. with shaking at 250 rpm. When OD=0.3, IPTG was added (final concentration of 1 mM) and continued to grow for 4 hours.

Preparation of crude extracts: 30 ml of the induced bacteria was collected by centrifuge at 4° C. The pellets were washed with pre-cold Tris-HCl (pH7.5) two times, and then suspended in 1.5 ml Tris-HCl (pH7.5). The cells were disrupted with Sonicator (SCIENTZ-II0, Ninbo Bcientz Biotechnology Co., Ltd, China), with an intensity of 25% for 3 min, sonicating for 1 sec and stopping for 1 sec. Finally, the disrupted cells were centrifuged at 4° C. 13,000 rpm for 15 min to remove debris.

Assay of the total protein concentration of crude extracts: the total protein concentration of crude extract was determined by Bio-Rad Protein Assay Kit (Bio-Rad, USA) according to the manufacturer's instruction.

PDH (pyruvate dehydrogenase) enzyme activity: Each 1 ml reaction mixture contained 100 mM Tris (pH 7.5), 10 mM $MgCl_2$, 1 mM DTT, 2.5 mM $NAD^+$, 0.2 mM TPP, 0.1 mM CoA, 5 mM sodium pyruvate, and 10 μl crude extract. The absorption of NADH at 340 nm was measured: the coefficient of NADH at 340 nm is 6.23 $cm^{-1}$ $mM^{-1}$. One unit of enzyme activity was defined as the production of 1 μmol NADPH $min^{-1}$ mg $protein^{-1}$ PDH sensitivity to NADH: the enzyme activity of PDH at $NADH/NAD^+$ different ratios was determined using the PDH activity reaction mixture with addition of NADH at a final concentration of 0 mM, 0.05 mM, 0.1 mM, 0.15 mM, 0.2 mM, 0.25 mM, 0.3 mM, or 0.35 mM (corresponding to $NADH/NAD^+$ ratio of 0, 0.02, 0.04, 0.06, 0.08, 0.1, 0.12, 0.14).

The results of PDH activity showed that for strains with single nucleotide mutation of lpdA, the PDH activity of E354K (pXZ165), T81I (pXZ173), P275S (pXZ178) and A358V (pXZ179) was 0.17, 0.085, 0.20 and 0.27 μmol/mg·min, respectively. The PDH activity of the strain with single nucleotide mutation A358V (pXZ179) was highest, which was 5.9-fold and 2.1-fold higher than control plasmid pTrc99A-M(0.046 μmol/mg·min) and wild type lpdA (pXZ163, 0.13 μmol/mg·min), respectively. For strains with double and triple nucleotide mutations, the PDH activity of P275SA358V (pXZ180) and T81IP275SA358V (pXZ174) were 0.22 and 0.24 μmol/mg·min, wherein the activity of the strain with triple nucleotide mutations was 1.85-fold higher than wild type lpdA (pXZ163).

Inhibition of high concentration of NADH: the PDH activity of strains containing wild-type lpdA (pXZ163), or lpdA with single mutation P275S (pXZ178) decreased to zero, when $NADH/NAD^+$ ratio was 0.12. The PDH activity of the strain containing lpdA with single mutation T81I (pXZ173) decreased to zero, when $NADH/NAD^+$ ratio was 0.04.

(FIG. 1)

When $NADH/NAD^+$ ratio was 0.14, the PDH activity of the strain containing lpdA with triple mutations T81IP275SA358V (pXZ174) was highest, 0.16 μmol/mg·min, being 67% of the activity when $NADH/NAD^+$ ratio was zero. When $NADH/NAD^+$ ratio was 0.14, the PDH activity of the strain containing lpdA with single mutation A358V (pXZ179) was 0.13 μmol/mg·min, being 48% of the activity when $NADH/NAD^+$ ratio was zero. When $NADH/NAD^+$ ratio was 0.14, the PDH activity of the strain containing lpdA with double mutations P275SA358V (pXZ180) was 0.08 μmol/mg·min, being 36% of the activity when $NADH/NAD^+$ ratio was zero. When $NADH/NAD^+$ ratio was 0.14, the PDH activity of other strains was zero.

Example 4

Production of Ethanol by Improving PDH Activity Under Anaerobic Condition (1) Construction of the Recombinant Strain ET-T006

(1-1): Plasmid pXZ-CS was Firstly Constructed for Gene Deletion, Modulation and Integration.

Four steps were applied to construct the plasmid pXZ-CS:

First step, a chloramphenicol resistance gene was amplified by using the plasmid pACYC184 DNA (Mok et al., 1991. Nucleic acids Res 19:2321-2323) as template with primers 184-cat-up/184-cat-down (SEQ ID No.: 19/SEQ ID No.: 20). The resulting PCR product with 994 bp was designated as fragment I, containing the chloramphenicol gene promoter sequence.

PCR system: 10 μl of New England Biolabs Phusion 5× buffer, 1 μl of dNTP (each dNTP, 10 mM), 20 ng of DNA template, and 2 μl of each primer (each of 10 μM), 0.5 μl of Phusion High-Fidelity DNA polymerase (2.5 U/μL), 33.5 μl of distilled water, in 50 μl of total volume.

PCR cycles: 1 cycle of 98° C. for 2 minutes (pre-denaturing); 30 cycles of 98° C. for 10 seconds (denaturing), 56° C. for 10 seconds (annealing), and 72° C. for 30 seconds (extension); 1 cycle of 72° C. for 5 minutes (extension).

Second step, a levansucrase gene (sacB) was amplified by using the chromosome DNA from *Bacillus subtilis* sp *subtilis* 168 (China General microbiological culture collection center, China. CGMCC No. 1.1390) as template with a primer set Bs-sacB-up/Bs-sacB-down (SEQ ID No.: 21/SEQ ID No.: 22). The resulting PCR product with 1618 bp was designated as fragment II, containing sacB gene promoter sequence. The PCR system and cycles were referred to the first step in the section (1-1) of Example 4.

Third step, fragment I obtained in the first step and fragment II obtained in the second step were digested with restriction endonuclease SacI (NEB) at 37° C. for 30 minutes. The digested products were cleaned using Purification Kit Cleaning Gel/PCR Extraction kit (BioMIGA Biotechnology Company). Each 20 ng of fragment I and fragment II were added with 1 µl of 10XT4 ligation buffer (NEB) and 1 µl of T4-DNA ligase (NEB), supplemented with distilled water to a final volume of 10 µl, and reacted at 25° C. for 5 minutes. Taking 1 µl of ligation product as template, fragment III containing cat-sacB cassette was amplified with a primer set 184-cat-up/Bs-sacB-down (SEQ ID No.: 19/SEQ ID No.: 22). The PCR system and cycles was referred to the first step in the section (1-1) of Example 4.

Fourth step, 1 µl of fragment III obtained from PCR was added into 1 µl of pEASY-blunt simple vector (Beijing TransGen Biotech, China.) and allowed for reaction at 25° C. for 15 min. CaCl$_2$ transformation was the same as that described in the section (1) of Example 2. 200 µl of transformed competent cells were plated onto a LB plate containing ampicillin (final concentration of 100 µg/mL) and chloramphenicol (final concentration of 34 µg/mL). The plate was incubated overnight, and 5 positive colonies were picked up for PCR verification with primers M13-F/M13-R (SEQ ID No.: 23/SEQ ID No.: 24). By sequencing analysis, the correct clone is positive clone and the plasmid was designated as pXZ-CS (Table 3).

(1-2): Deletion of ldhA gene (GenBank No: ACA77176.1) from *E. coli* ATCC 8739 to obtain recombinant *E. coli* Suc-T102

Starting from *E. coli* ATCC 8739, two-step homologous recombination was applied to delete ldhA gene to obtain recombinant *E. coli* Suc-T102, including the following six steps.

First step, taking the chromosome DNA from *E. coli* ATCC 8739 as template, a PCR product of 1753 bp was amplified with a primer set XZ-ldhA-up (SEQ ID No.: 25/SEQ ID No.: 26), containing lactate dehydrogenase gene ldhA (GenBank accession No: ACA77176.1) of *E. coli* ATCC 8739 and its upstream and downstream sequences of about 400 bp. The PCR system and cycles were referred to first step in the section (1-1) of Example 4.

The amplified PCR product of 1753 bp was cloned into the pEASY-Blunt cloning vector (Beijing TransGen Biotech). The cloning system is the same as described in the section (1-1) of Example 4, and calcium chloride transformation is the same as the section (1) of Example 2. 200 µl of transformed competent cells were plated onto a LB plate containing kanamycin (final concentration of 15 µg/ml), and grown for overnight. 5 positive colonies were verified by colony PCR with a primer set M13-F/M13-R (SEQ ID No.: 23/SEQ ID No.: 24) and sequenced, and the plasmid from the correct one was designated as pXZ-001.

Second step, PCR amplification was carried out by using the DNA of the plasmid pXZ001 as template with primers XZ-ldhA-1/XZ-ldhA-2 (SEQ ID No.: 27/SEQ ID No.: 28), and the PCR product of 4758 bp was obtained containing pEASY-Blunt vector as well as each of the upstream and downstream sequences of IdhA gene of about 400 bp. The PCR system and cycles were referred to the first step in the section (1-1) of Example 4.

Third step, the DNA fragment cat-sacB containing chloramphenicol gene (cat) and levansucrase gene (sacB) was ligated into the PCR amplified product of the second step. The details were as follows:

taking pXZ-CS as template, a PCR product of 2618 bp was amplified with a primer set cat-sacB-up (SEQ ID No.: 29)/cat-sacB-down (SEQ ID No.: 30). The PCR product with 2618 bp contained chloramphenicol gene (cat) and levansucrase gene (sacB).

Ligation System: 10 ng of the 4758 bp PCR product obtained in the second step, 30 ng of the cat-sacB cassette DNA fragment and 2 µl of 10×T4 DNA ligation buffer (NEB), 1 µl of T4 ligase (NEB, 400,000 cohesive end units/mL), distilled water added to a final total volume of 20 µl. The ligation was at room temperature for 2 hours. The CaCl$_2$ transformation is the same as the section (1) of Example 2. 200 µl of the transformed competent cells were plated onto a LB plate containing chloramphenicol (final concentration of 17 µg/mL), and grown for overnight. 5 positive single colonies were picked up. The positive colonies were cultured in liquid medium and the plasmid (cat-sacB DNA fragment was cloned into the plasmid pXZ001) was extracted for sequencing. The sequencing results showed that cat-sacB DNA fragment was ligated to the PCR product in the above second step, demonstrating the correct construction of the plasmid and the resulting recombinant plasmid was designated as pXZ002C.

Fourth step, taking the DNA of plasmid pXZ002C as template, a PCR fragment I (3447 bp) was amplified with primers XZ-ldhA-up/XZ-ldhA-down (SEQ ID No.: 25/SEQ ID No.: 26). The PCR system and cycle were referred to the first step described in the section (1-1) of Example 4. The DNA fragment I contained 400 bp upstream of lactate dehydrogenase gene ldhA, cat-sacB cassette, and 400 bp downstream of lactate dehydrogenase gene ldhA.

The DNA fragment I was used for the first homologous recombination. Plasmid pKD46 (Wanner and Datsenko 2000, Proc Natl Acad SCI USA 97:6640-6645) was firstly transformed into *E. coli* ATCC 8739 by CaCl$_2$ transformation, and then the DNA fragment I was electroporated into *E. coli* ATCC 8739 harboring the pKD46.

Electroporation Program: first, electroporation competent cells of *E. coli* ATCC 8739 harboring the pKD46 were prepared by the method described by Dower (Dower et al., 1988. Nucleic Acids Res 16:6127-6145). 50 µl of competent cells were placed on ice, added with 50 ng of the DNA fragment I, and then placed on ice for 2 minutes. The mixture of the DNA and the cells were transferred into a 0.2 cm Bio-Rad cuvette. The electric voltage was 2.5 KV by the MicroPulser (Bio-Rad) electroporation apparatus. After shocks, 1 mL of LB medium were quickly added into the electroporation cuvette and transferred into a tube after pipetting five times. The culture was incubated at 30° C. with shaking at 75 rpm for two hours. 200 µl of culture was spread onto a LB plate containing chloramphenicol (final concentration of 17 µg/mL), and incubated at 37° C. overnight. 5 colonies were verified by PCR with a primer set XZ-ldhA-up/XZ-ldhA-down (SEQ ID No.: 25/SEQ ID No.: 26). A correct colony was designated as Suc-T101.

Fifth step, the 4758 bp PCR product obtained in the second step was phosphorylated, and the self-ligated plasmid was used for the second homologous recombination. Specifically, the 4758 bp PCR product was cleaned up with PCR purification Kit (Gel/PCR Extraction Kit, BioMIGA). 20 µl of reaction volume included 30 ng of the purified PCR product, 2 µl of 10XT4 ligation buffer (NEB), 1 µl of T4 polynucleotide kinase (NEB), and remaining distilled water were reacted at 37° C. for 30 minutes. 1 μl of T4 ligase (NEB, 400,000 cohesive end units/ml) was added and reacted at room temperature for 2 hours to obtain ligation product. The CaCl₂ transformation is the same as the section (1) of Example 2. 200 μl of transformed competent cells were spread onto a LB plate containing kanamycin (final concentration of 15 μg/mL) and incubated for overnight. 5 positive single colonies were picked up and cultured in liquid medium for extracting plasmid for sequencing. The sequencing results showed the PCR product in the second step was self-ligated, showing correct construction of the plasmid. The resulting plasmid was designated as pXZ003.

Sixth step, an 829 bp DNA fragment II was amplified by using the plasmid pXZ003 as template with primers XZ-ldhA-up/XZ-ldhA-down (SEQ ID No.: 25/SEQ ID No.: 26) for second homologous recombination. The DNA fragment II was electroporated into the strain Suc-T101.

Electroporation Program: first, electroporation competent cells of Suc-T101 harboring plasmid pKD46 were prepared. 50 μl of competent cells were placed on ice, added with 50 ng of the DNA fragment II, and then placed on ice for 2 minutes. The mixture of the DNA and cells were transferred into a 0.2 cm Bio-Rad cuvette. The electric voltage was 2.5 KV applied by the MicroPulser (Bio-Rad) electroporation apparatus. After shock, 1 mL of LB medium was quickly added into the electroporation cuvette and transferred into a tube after pipetting five times. The culture was incubated at 30° C. with shaking at 75 rpm for 4 hours to remove the plasmid pKD46. The culture was then transferred to LB liquid medium with 10% sucrose but without sodium chloride (50 mL medium in 250 mL flask), cultured for 24 hours and then streaked on LB solid medium with 6% sucrose but without sodium chloride and incubated. The correct colony amplification product was a 763 bp fragment via PCR verification with a primer set XZ-ldhA-up/XZ-ldhA-down (SEQ ID No.: 25/SEQ ID No.: 26). A correct one was designated as Suc-T102 (Table 1).

The plasmids constructed for deletion of ldhA gene are listed in Table 3, and the primers used are listed in Table 2.

(1-3) The pflB gene (GenBank No: ACA78322.1) from the recombinant E. coli Suc-T102 was deleted using the same method as described in the section (1-2) of Example 4, resulting in recombinant E. coli Suc-T104. The constructed plasmids are listed in Table 3, and the primers used are listed in Table 2. The primers were named in same manner used for deleting the ldhA gene, while only ldhA was replaced by pflB.

(1-4) The frdABCD gene (frdA GenBank No:ACA79460.1, frdB GenBank No:ACA79461.1, frdC GenBank No:ACA79462.1, frdD GenBank No:ACA79463.1) from the recombinant E. coli Suc-T104 was deleted using the same method as described in the section (1-2) of Example 4, resulting in recombinant E. coli ET-T006. The plasmids constructed are listed in Table 3, and the primers used are listed in Table 2. The primers were named in same manner used for deleting the ldhA gene, in which XZ-ldhA-up, XZ-ldhA-down, XZ-ldhA-1 and XZ-ldhA-2 were replaced by XZ-frdB-up, XZ-frdC-down, XZ-frdC-1, and XZ-frdB-2, respectively.

(2) Construction of Recombinant E. coli JC-009

The lpdA* gene was integrated at ackA-pta site in chromosome of the recombinant E. coli ET-T006, resulting in the recombinant E. coli JC007. lpdA* was then modulated by the artificial regulation part M1-93 (SEQ ID No.: 6) to obtain recombinant strain JC-009. The specific steps are as follows.

First step, construction of the integration vector pTrc99A-M-Kan.

Specifically, taking the DNA of plasmid pKD4 (Datsenko and Wanner 2000, Proc Natl Acad Sci USA 97:6640-6645; pKD4 from CGSC E. coli culture collection center of Yale University) as template, a FRT-km fragment was amplified with a primer set Kan-up-PacI/Kan-down-EcoRI (SEQ ID No.: 39/SEQ ID No.: 40). The PCR system and cycles were referred to the first step in the section (1-1) of Example 4. The FRT-km fragment was digested with restriction endonuclease PacI/EcoRI (NEB) at 37° C. for 30 minutes, and pTrc99A-M (Zhao et al 2013, Met Eng 17:42-50, constructed by our lab, having the sequence of SEQ ID NO: 111) was digested with the same endonuclease. The digested products were cleaned using Purification Kit Cleaning Gel/PCR Extraction kit (BioMIGA Biotechnology Company). The cleaned fragments FRT-km and pTrc99A-M were ligated. The Cloning system and CaCl₂ transformation were as described in section (1) of Example 2. Transferring 200 μl of transformed competent cells onto LB plate containing kanamycin (final concentration of 50 μg/mL) and ampicillin (final concentration of 50 μg/mL), and grown for overnight. Plasmids from 2-3 colonies were verified by colony PCR with a primer set Kan-F/pTrc99A-R (SEQ ID No.: 41/SEQ ID No.: 18) and sequencing. The correct one was designated as pTrc99A-M-Kan.

Second step, the lpdA* gene was cloned into pTrc99A-M-Kan to obtain plasmid pXZ177.

Specifically, the plasmid pXZ174 was digested with restriction endonucleases SacI/HindIII (NEB) at 37° C. for 30 minutes, and the fragment lpdA* of 1455 bp in size was recovered. The pTrc99AM-Kan was digested with the same enzymes. The digested products were cleaned using Purification Kit Cleaning Gel/PCR Extraction kit (BioMIGA Biotechnology Company). The cloning system and CaCl₂ transformation were the same as described in the section (1) of Example 2. Transferring 200 μl of transformed competent cells onto a LB plate containing kanamycin (final concentration of 50 μg/mL) and ampicillin (final concentration of 100 μg/mL) and grown for overnight. 5 positive single colonies were picked up and validated by colony PCR with a primer set Kan-F (SEQ ID No.: 41)/lpdA-R-170 (SEQ ID No.: 44). The sequencing results showed correct construction of the plasmid, designated as pXZ177.

Third step, the lpdA* fragment was integrated into ackA site of the recombinant E. coli ET-T006 to obtain the recombinant E. coli JC-007.

Preparation of the fragment for one-step recombination: a PCR fragment form plasmid pXZ177 was amplified with a primer set ackA-FRT-up/pta-rrnB-down (SEQ ID No.: 42/SEQ ID No.: 43) to obtain the fragment for one-step recombination containing 50 bp left homologous arm of ackA, FRT-km-lpdA* sequence and 50 bp right homologous arm of ackA.

The fragment for one-step recombination was then electrotransformed into ET-T006 harboring plasmid pKD46. The electroporation program was the same as that in the section (1-2) of Example 4. 200 μl of transformed competent cells was plated onto LB plate containing kanamycin (final concentration of 50 μg/mL), and grown at 37° C. for overnight. 5 single colonies were verified by colony PCR with a primer set XZ-ackA-up/lpdA-R-170 (SEQ ID No.: 76/SEQ ID No.: 44). The correct one was designated as JC007.

Fourth step, lpdA* gene from JC-007 was modulated by the artificial regulatory part M1-93 (SEQ ID No.: 6) using two-step homologous recombination, resulting in recombinant E. coli JC009.

Taking plasmid pXZ-CS as template, DNA fragment I was amplified with a primer set ackA-cat-sacB-up/lpdA-cat-sacB-down (SEQ ID No.: 45/SEQ ID No.: 46). The PCR system and cycles refer to the first step in the section (1-1) of Example 4. The resulting DNA fragment I of about 3 kb contained left homologous arm of ackA of 50 bp, cat-sacB cassette and right homologous arm of lpdA of 50 bp.

The method for the first recombination was the same as described in the section (1-2) of Example 4. The ackA-pta gene of JC-007 was replaced with cat-sacB cassette of the DNA fragment I, resulting in strain JC-009a.

Taking genome DNA of recombinant E. coli M1-93 (Lu et al., 2012, Appl Microbiol Biotechnol. 93:2455-2462) as template, DNA fragment II was amplified with a primer set ackA-P-up/lpdA-RBS-down (SEQ ID No.: 47/SEQ ID No.: 48). The PCR system and cycles refer to the first step in the section (1-1) of Example 4. The obtained DNA fragment II of about 200 bp contained left homologous arm of ackA of 50 bp, M1-93 promoter fragment and right homologous arm of lpdA of 50 bp.

The method for the second recombination was the same as described in the section (1-2) of Example 4. The cat-sacB gene of JC-009a was replaced by the DNA fragment II, resulting in recombinant strains. The strains were verified by PCR with primers AP1-up/lpdA-R-170 (SEQ ID No.: 56/SEQ ID No.: 44), and the correct one was designated as JC-009 (Table 1).

(3) Fermentation of Recombinant Strains ET-T006 and JC-009

The components of seed medium and fermentation medium consist of ($H_2O$ as solvent):

Major elements: glucose 50 g/L, $KH_2PO_4$ 3.9 g/L, $K_2HPO_4$ 5.85 g/L, $(NH_4)_2HPO_4$ 3.5 g/L, $MgSO_4.7H_2O$ 0.37 g/L, and Betaine-KCl 0.15 g/L; and Trace elements: $FeCl_3.6H_2O$ 1.5 µg/L, $CoCl_2.6H_2O$ 0.1 µg/L, $CuCl_2.2H_2O$ 0.1 µg/L, $ZnCl_2$ 0.1 µg/L, $Na_2MoO_4.2H_2O$ 0.1 µg/L, $MnCl_2.4H_2O$ 0.1 µg/L, and $H_3BO_3$ 0.05 µg/L.

Anaerobic fermentation of strains ET-T006 and JC-009 to produce ethanol was carried out as follows:

(a) Seed culture: 100 ml of seed medium in a 250 ml flask was sterilized at 115° C. for 15 min. E. coli JC-009 was grown by transferring pre-inocula into the seed medium with an inoculum of 1% (v/v), at 37° C. shaking with 100 rpm for 12 hours to obtain seed culture;

(b) Fermentation culture: the seed cultures were diluted into a 500-ml fermentation vessel containing 250 ml fermentation medium with a final concentration of $OD_{550}$=0.1. Fermentations were grown at 37° C. for 3 days to obtain fermentation broth. No air was sparged in whole processes for fermentation. The fermentation broth comprises all the substance in the vessel.

Analysis: the components in the fermentation broth were measured by using High-Performance Liquid Chromatography (Agilent-1200). The concentrations of glucose, ethanol and organic acids were measured by using the column of Aminex HPX-87H (Bio-rad).

PDH activity assay: (a) preparation of crude extracts: 15 ml of the fermentation broth at exponential phase was collected by centrifuge at 4° C. The pellet was washed with pre-cold Tris-HCl (pH7.5) two times, and then suspended in 1.5 ml Tris-HCl (pH7.5). The cells were disrupted with Sonicator (SCIENTZ-II0, Ninbo Bcientz Biotechnology Co., Ltd, China), with an intensity of 25% for 3 min, sonicating for 1 sec and stopping for 1 sec. Finally, the disrupted cells were centrifuged at 4° C. 13,000 rpm for 15 min to remove debris. (b) determination of the total protein concentration in the crude extract: the total protein concentration in the crude extract was determined by using Bio-Rad Protein Assay Kit (Bio-Rad, USA) according to the manufacturer's instruction. (c) Each 1 ml reaction mixture contained 100 mM Tris (pH 7.5), 10 mM $MgCl_2$, 1 mM DTT, 2.5 mM $NAD^+$, 0.2 mM TPP, 0.1 mM CoA, 5 mM pyruvate and 10 µl of the crude extract. The absorption of NADH at 340 nm was measured: the coefficient of NADH is 6.3 $mM^{-1}cm^{-1}$. One unit of enzyme activity was defined as the production of 1 µmol NADPH $min^{-1}$ mg $protein^{-1}$.

The results of fermentation were shown in Table 4. After 96 h fermentation, the strain ET-T006 produced 5.8 mM of ethanol with a yield of ethanol of 0.28 mol/mol. The enzyme activity of pyruvate dehydrogenase was 0.15 µmol/mg/min.

After 96 h fermentation, the strain JC-009 produced 12.8 mM of ethanol with a yield of ethanol of 0.34 mol/mol. The enzyme activity of pyruvate dehydrogenase was 0.33 µmol/mg/min.

(4) Construction and Fermentation of Recombinant E. coli JC-015

Starting from the recombinant E. coli JC-007, lpdA* was modulated with RBS library by two-step homologous recombination. The process comprised the following three steps:

First step, in the homologous recombination, ackA-pta gene in JC-007 was replaced by cat-sacB cassette to obtain strain JC-009a. The method was the same as described in section (1-2) of Example 4.

Second step, taking genome DNA of the strain JC-009 as template, the fragments of RBS library for the second homologous recombination was amplified with a primer set ackA-up-500/lpdA-RBSL-down (SEQ ID No.: 49/SEQ ID No.: 50). The electroporation program was the same as described in section (1-2) of Example 4. The colonies obtained were verified by colony PCR with a primer set AP1-up/lpdA-R-170 (SEQ ID No.: 56/SEQ ID No.: 44). Ten correct colonies were selected for fermentation.

Third step, the fermentation of the ten strains was carried out using the method as described in section (3) of Example 4.

Figure 2:
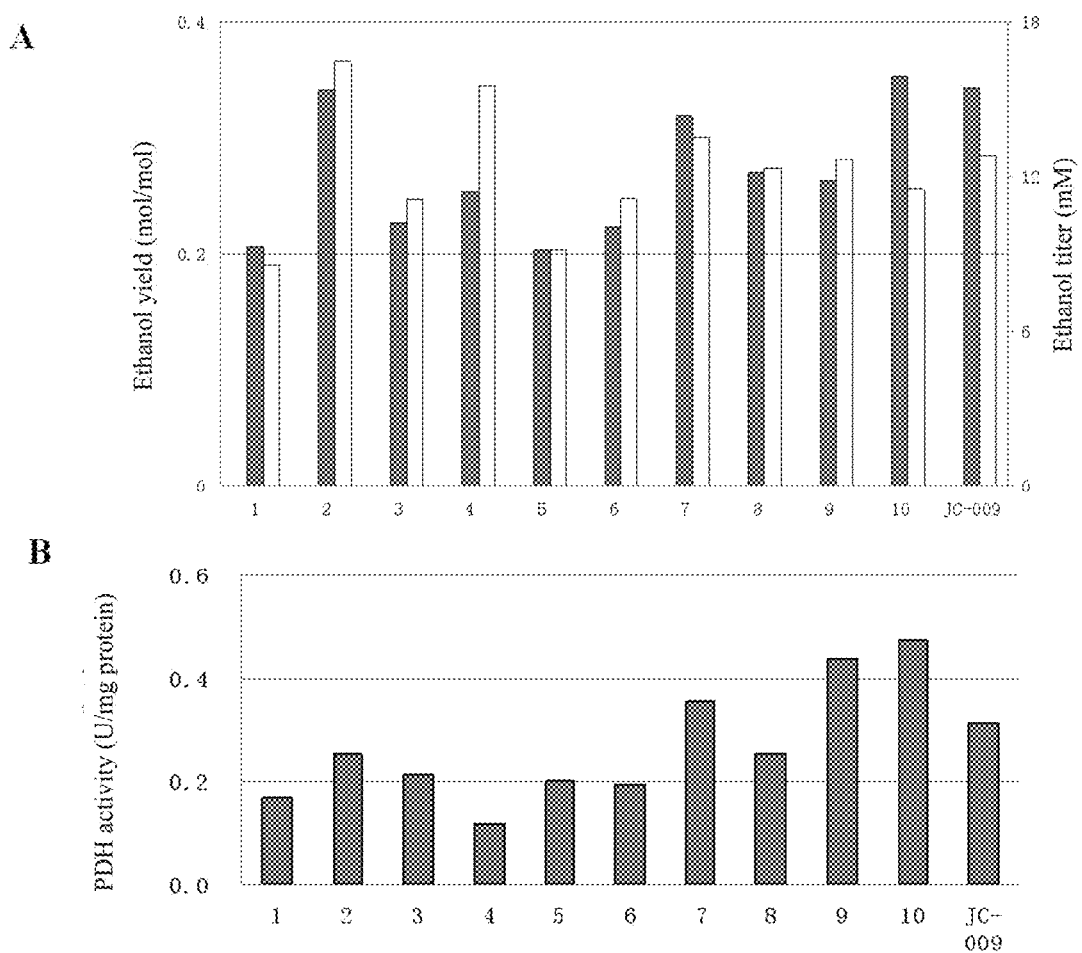
FIG. 2: The anaerobic fermentation results of 10 colonies from lpdA* gene RBS library of JC-007. (A) The ethanol titer and yield; (B) PDH activity assay.

The results of fermentation were shown in Table 4 and FIG. 2. Among the ten strains, the No. 10 strain that was designated as JC-015 had the highest PDH activity of 0.48 µmol/mg/min. After 96 h fermentation, JC-015 produced 11.5 mM of ethanol with a yield of 0.35 mol/mol.

After introducing lpdA* gene and increasing its expression strength, the PDH activity of the obtained recombinant E. coli JC-015 in anaerobic condition was increased 3.2-fold, and the ethanol titer increased 2-fold with a yield increased 25%, comparing to the parent strain ET-T006.

The RBS regulatory part of lpdA* gene in JC-015 was sequenced, and designated as RBSL10 (SEQ ID No.: 80).

(5) Construction and Fermentation of Recombinant Strain JC-018

The aceEF gene from recombinant E. coli JC-015 was modulated with RBS library regulatory parts by one-step homologous recombination.

First step, taking the genome DNA of the recombinant E. coli M1-93 as template, the fragments of RBS library for the homologous recombination were amplified with a primer set aceEF-FRT-up/aceEF-RBSL-down (SEQ ID No.: 57/SEQ ID No.: 58). The amplification system and cycles were the same as described in the first step in the section (1-1) of Example 4.

Second step, the obtained DNA fragments were transformed into JC-015 with pKD46 by electroporation as described in section (1-2) of Example 4. The colonies obtained were verified by PCR using a primer set aceEF-1/Ap1-up (SEQ ID No.: 55/SEQ ID No.: 56). Ten correct colonies were chosen for further fermentation.

The fermentation of the ten strains was carried out using the method as described in section (3) of Example 4.

Figure 3:
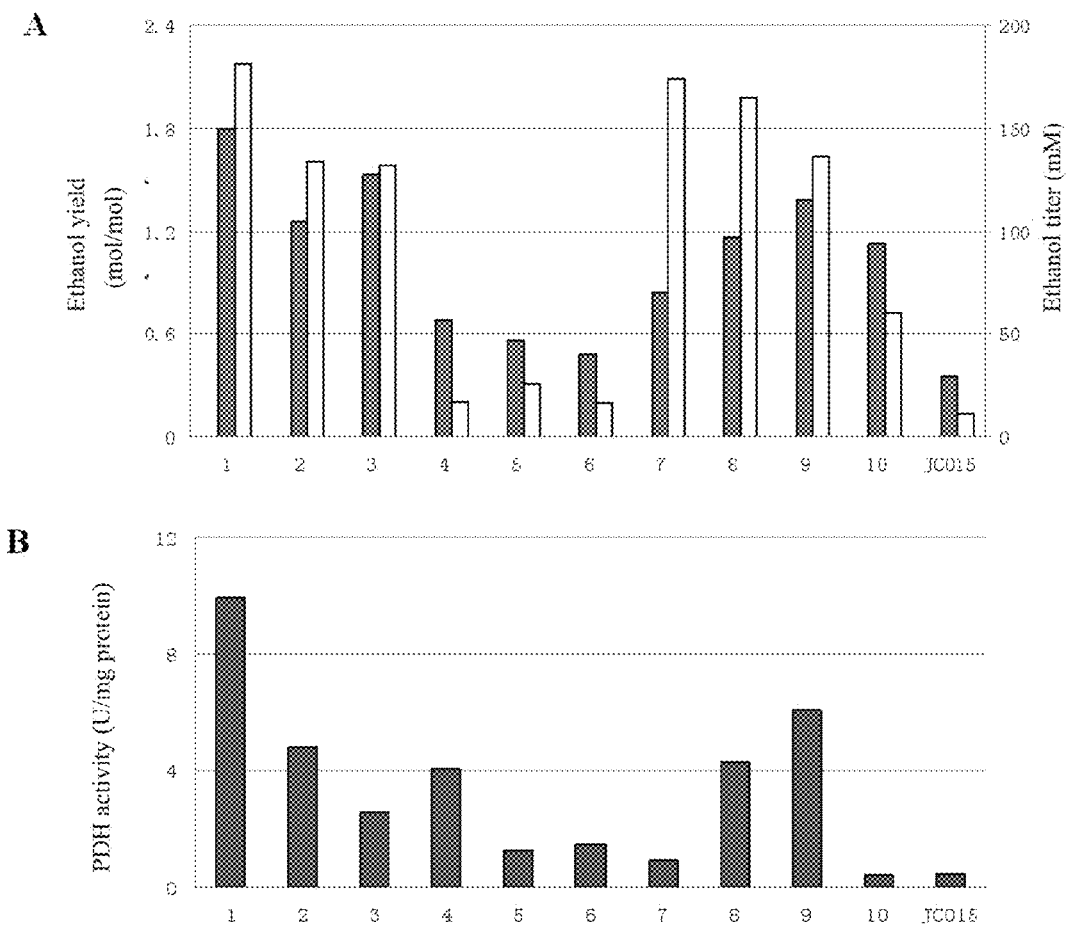
FIG. 3: The anaerobic fermentation results of 10 colonies from aceEF gene RBS library of JC-015. (A) The ethanol titer and yield; (B) PDH activity assay.

The results of fermentation were shown in Table 4 and FIG. 3. Among the ten strains, the strain No. 1 that was designated as JC-018 had the highest PDH activity of 9.9 µmol/mg/min. After 96 h fermentation, JC-018 produced 181.1 mM ethanol with a yield of 1.8 mol/mol (Table 4).

After introduction of lpdA* gene and increasing the expression strength of lpdA* and aceEF genes, the PDH activity of the obtained recombinant E. coli JC-018 was increased 66-fold under anaerobic condition, and the ethanol titer increased 31-fold with a yield increased 6.4-fold, comparing to the parent strain ET-T006.

The RBS regulatory part of aceEF gene in JC-018 was sequenced, and designated as RBSL1 (SEQ ID No.: 81).

(6) Construction and Fermentation of Recombinant Strain JC-019

The aceEF gene from recombinant E. coli ET-T006 was modulated with the optimal regulatory part RBSL1 (SEQ ID No.: 81) from the RBS library of aceEF gene in JC-018.

First step, taking the genome DNA of E. coli JC-018 as template, the regulatory fragment I, RBSL::aceEF for one-step homologous recombination was amplified with a primer set aceEF-up-500/aceEF-1 (SEQ ID No.: 59/SEQ ID No.: 55). The amplification system and cycles refer to those as described in the first step in section (1-1) of Example 4.

Second step, the amplified DNA fragments obtained were electroporated into the strain ET-T006 with the plasmid pKD46. The electroporation program was the same as described in section (1-2) of Example 4. 300 µl of transformed competent cells were plated onto a LB plate containing kanamycin, and incubated at 37° C. overnight. The colonies were verified by PCR with a primer set kan-F/aceEF-1 (SEQ ID No.: 41/SEQ ID No.: 55). The correct colony was designated as JC-019.

The fermentation of JC-019 was carried out using the method as described in section (3) of Example 4.

The results of fermentation were shown in Table 4. The PDH activity of the strain JC-019 was 7.5 µmol/mg/min. After 96 h fermentation, JC-019 produced 121 mM ethanol with a yield of 1.33 mol/mol (Table 4).

After increasing the expression strength of aceEF gene, the PDH activity of the obtained recombinant E. coli JC-019 was increased by 50-fold under anaerobic condition, and the ethanol titer was increased 21-fold with a yield increased 4.8-fold, comparing to the recombinant strain ET-T006.

Strain JC-018, in comparison to JC-019, had an additional lpdA* gene integration and enhanced expression strength of lpdA* gene, whose PDH activity was increased 32% under anaerobic condition, ethanol titer increased 50% with a yield of 35% increase.

TABLE 4

Anaerobic fermentation of strains ET-T006, JC-009, JC-015, JC-018 and JC-019

| Strain | Genetic modification | Time (day) | Cell mass (g/L) | PDH activity (U/mg protein) | Ethanol yield (mol/mol) | Fermentation products (mM) | |
|---|---|---|---|---|---|---|---|
| | | | | | | ethanol | acetate |
| ET-T006 | | 4 | 0.14 | 0.15 ± 0.02 | 0.28 ± 0.01 | 5.8 ± 0.3 | 3.4 ± 0.1 |
| JC-009 | ET-T006, ackA::M1-93-lpdA* | 4 | 0.17 | 0.33 ± 0.03 | 0.34 ± 0.01 | 12.8 ± 0.4 | 4.2 ± 0.2 |
| JC-015 | ET-T006, ackA::RBSL10-lpdA* | 4 | 0.20 | 0.48 ± 0.05 | 0.35 ± 0.01 | 11.5 ± 0.4 | 0 |
| JC-019 | ET-T006, RBSL1-aceEF | 4 | 0.53 | 7.5 ± 0.2 | 1.33 ± 0.04 | 121 ± 3.9 | 0 |
| JC-018 | ET-T006, ackA::RBSL10-lpdA*, RBSL1-aceEF | 4 | 0.54 | 9.9 ± 0.3 | 1.80 ± 0.05 | 181 ± 3.3 | 0 |

Example 5

Improving PDH Activity for Succinate Production Under Anaerobic Condition (1) Construction of Recombinant E. coli Suc-T110

(1-1) The ptsI gene (GenBank No: ACA76928.1) from strain Suc-T104 was deleted by the method as described in section (1)1.2 of Example 4, resulting in recombinant E. coli strain Suc-T106. The plasmids constructed are listed in Table 3, and the primers used are listed in Table 2. The primers were named in same manner used for deleting the ldhA gene, while only ldhA was replaced by ptsI.

(1-2) The native promoter of galP gene (GenBank No: ACA76443.1) from strain Suc-T106 was replaced the mutated Ppck*, resulting in strain Suc-T108. In the invention, Ppck* represents mutated pck promoter, i.e. containing G to A transition at position −64 relative to the ATG start codon (Zhang al. 2009b, Appl Environ Microbiol 75:7807-7813).

The process comprised the following six steps.

First step, taking genomic DNA of E. coli ATCC 8739 as template, an amplification product of 841 bp was amplified with a primer set XZ-galP-P-up/XZ-galP-P-down (SEQ ID No.: 64/SEQ ID No.: 65). The resulting PCR product with 841 bp contained galP gene's promoter of E. coli ATCC 8739 and its upstream and downstream sequences of about 400 bp, respectively. The amplification product was cloned into pEASY-Blunt cloning vector. The positive plasmids were extracted for sequencing. The sequencing results showed that the regulatory element of galactose transporter gene galP and its upstream and downstream sequences of about 400 bp were inserted into the vector pEASY-Blunt, showing correct construction of the plasmid. The resulting recombinant plasmid was designated as pXZ011

Second step, taking DNA of plasmid pXZ011, an amplification product of 4614 bp was amplified with a primer set XZ-galP-P-1/XZ-galP-P-2 (SEQ ID No.: 66/SEQ ID No.: 67). The resulting product with 4614 bp contained the sequence of pEASY-Blunt vector, the promoter of galP gene and its upstream and downstream sequences of about 400 bp.

Third step, taking plasmid pXZ-CS as template, a PCR fragment of 2618 bp was amplified with a primer set cat-sacB-up/cat-sacB-down (SEQ ID No.: 29/SEQ ID No.: 30), containing chloramphenicol gene (cat) and levansucrase gene (sacB).

The DNA fragment containing chloramphenicol gene (cat) and levansucrase gene (sacB) was ligated into the amplification product of 4614 bp obtained in the second step. The ligation system and $CaCl_2$ transformation were the same as described in section (1) of Example 2. 200 μl of transformed competent cells were plated onto a LB plate containing chloramphenicol (final concentration of 17 μg/mL), and grown for overnight. 5 positive single colonies were picked up and cultured in liquid medium and then the plasmid (in which the cat-sacB fragment was cloned into pXZ010) was extracted for sequencing. The results showed that the amplification product obtained in the second step was ligated with the cat-sacB fragment, showing correct construction of the plasmid. The resulting recombinant plasmid was designated as pXZ012C.

Fourth step, taking DNA of plasmid pXZ012C as template, DNA fragment I (3303 bp) was amplified with a primer set XZ-galP-P-up/XZ-galP-P-down (SEQ ID No.: 64/SEQ ID No.: 65), containing 400 bp upstream of galP's promoter, cat-sacB cassette, 400 bp downstream of galP's promoter.

DNA fragment I was used for the first homologous recombination. The plasmid pKD46 was transformed to strain Suc-T106 by $CaCl_2$ transformation, and then the DNA fragment I was electroporated to the strain Suc-T106 harboring pKD46.

The electroporation program was referred to section (1-2) of Example 4. 200 μl of transformed competent cells were plated onto a LB plate containing chloramphenicol (final concentration of 17 μg/mL), and grown at 37° C. for overnight. 5 single colonies were verified by PCR using a primer set XZ-galP-P-up/XZ-galP-P-down (SEQ ID No.: 64/SEQ ID No.: 65). The correct one was designated as Suc-T107.

Fifth step, taking genomic DNA of E. coli ATCC 8739 as template, the native promoter of pck gene of E. coli ATCC 8739 was amplified with a primer set P-pck*-up-SpeI/P-pck*-down-KpnI (SEQ ID No.: 68/SEQ ID No.: 69). The primers are listed in Table 2. The PCR product was cleaved with SpeI (NEB) and KpnI (NEB), and cloned into the expression vector pTrc99A (Amann et al., 1998, Gene 69:301-15) cleaved with the same enzymes. The resulting plasmid was designated as pXZ602. Taking plasmid pXZ602 as template, PCR amplification was carried out with a primer set pck*-F/pck*-R (ID No. SEQ: 70/ID No. SEQ: 71). The primers are listed in Table 2. The amplification product was phosphorylated by T4 polynucleotide kinase (NEB), and then self-ligated, resulting in plasmid pXZ603.

Taking pXZ603 as template, a 378 bp mutated Ppck* of phosphoenolpyruvate carboxykinase PCK was amplified with a primer set P-pck*-up-SpeI/P-pck*-down-KpnI (SEQ ID No.: 68/SEQ ID No.: 69), and was ligated with the 4614 bp fragment prepared above in second step, resulting in plasmid pXZ013.

Taking plasmid pXZ013 as template, DNA fragment II was amplified using a primer set XZ-galP-P-up/XZ-galP-P-down (SEQ ID No.: 64/SEQ ID No.: 65).

Sixth step, DNA fragment II was used in the second homologous recombination. DNA fragment II was electroporated into Suc-T107. The electroporation program was the same as section (1-2) of Example 4. PCR was carried out using a primer set XZ-galP-P-up/XZ-galP-P-down (SEQ ID No.: 64/SEQ ID No.: 65), and then sequencing, to obtain correct colonies (1051 bp), which was designated as Suc-T108 (Table 1).

The plasmids used for replacing the native promoter of galp by Ppck* are listed in Table 3, and the primers used are listed in Table 2.

(1-3) The native promoter of pck gene (GenBank No: ACA75988.1) from recombinant E-coli Suc-T108 was replaced by Ppck* to obtain recombinant E-coli Suc-T110.

Specifically, the first homologous recombination: taking plasmid pXZ-CS as template, DNA fragment I (2717 bp) for the first homologous recombination was amplified with a primer set pck-cat-sacB-up/pck-cat-sacB-down (SEQ ID No.: 72/SEQ ID No.: 73). The primers used are listed in Table 2. The obtained DNA fragment I was electroporated into Suc-T108 harboring pKD46. The colonies with ampicillin- and chloramphenicol-resistance were intermediate recombination bacteria.

The second homologous recombination: taking plasmid pXZ603 as template, artificial regulatory part Ppck* (378 bp) was amplified with a primer set P-pck*-up-SpeI/P-pck*-down-KpnI (SEQ ID No.: 68/SEQ ID No.: 69) (primers listed in Table 2). This 378 bp artificial regulatory part Ppck* was electroporated into the intermediate recombination strain with fragment I integration to obtain recombinant bacterium 1. The resulting recombinant bacterium 1 was verified by PCR with a primer set pck-YZ-up/pck-YZ-down (SEQ ID No.: 74/SEQ ID No.: 75). After sequencing, the correct strain (676 bp) was designated as Suc-T110.

(2) Construction of Recombinant E. coli NZ-038

The lpdA* was integrated at ackA site in Suc-T110 to obtain recombinant E. coli NZ-038b. Then, the expression of lpdA* was modulated by artificial regulatory part M1-93 (SEQ ID No.: 6) to obtain recombinant E. coli strain NZ-038. The process was the same as described in section (2) of Example 4. The primers are listed in Table 2.

(3) Construction of Recombinant E. coli NZ-035

The phosphotransacetylase gene pta (GenBank No:ACA77021.1) and acetate kinase gene ackA (GenBank No:ACA77022.1) from Suc-T110 were deleted according to the method as described in section (1-2) of Example 4 to obtain recombinant E. coli NZ-035. The plasmids constructed are listed in Table 3, and the primers used are listed in Table 2. The primers were named in same manner used for deleting the ldhA gene, while only ldhA was replaced by ackA or pta, respectively. The primer set XZ-ackA-2/XZ-pta-2 (SEQ ID No.: 78/SEQ ID No.: 79) was used for inside-out PCR with the plasmid pXZ-023 as template.

(4) Construction of Recombinant E. coli NZ-041

Using two-step homologous recombination, the native promoter of aceEF gene from NZ-038 was replaced with the artificial regulatory part M1-93 (SEQ ID No.: 6), resulting in strain NZ-041. The method was the same as described in the fourth step of Example 4 (2). The primers used are listed in Table 2. The primers were named in same manner as those used for modulating lpdA* gene, while only ack or lpdA was replaced by aceEF.

(5) Construction of Recombinant *E. coli* NZ-099

The lpdA* gene was integrated at ackA site in strain Suc-T110 according to the method described in section (2) of Example 4, and then lpdA* was modulated by the optimal regulatory part RBSL10 (SEQ ID No.: 80) from the lpdA* gene library. RBSL10-lpdA* for the second homologous recombination was amplified using the genome DNA of JC-015 as template with a primer set ackA-up-500/lpdA-R-170 (SEQ ID No.: 49/SEQ ID No.: 44), resulting in strain NZ-099. The primers used are listed in Table 2.

(6) Construction of Recombinant *E. coli* NZ-098

The aceEF from strain Suc-T110 was modulated with the optimal regulatory part RBSL1 from the RBS library of aceEF gene, resulting in strain NZ-098. The method was the same as described in Example 4(6). The primers used are listed in Table 2.

(7) Construction of Recombinant *E. coli* NZ-100

The aceEF from strain NZ-099 was modulated with the optimal regulatory part RBSL1 from the RBS library of aceEF gene, resulting in strain NZ-100. The method was the same as described in Example 4(6). The primers used are listed in Table 2.

(8) Fermentation of Strains Suc-T110, NZ-035, NZ-038, NZ-041, NZ-098, NZ-099, and NZ-100

Seed medium consists of ($H_2O$ as solvent):

Major elements: glucose 20 g/L, $KH_2PO_4$ 3.5 g/L, $K_2HPO_4$ 6.55 g/L, $(NH_4)_2HPO_4$ 3.5 g/L, $MgSO_4.7H_2O$ 0.12 g/L, and Betaine-KCl 0.15 g/L, and Trace elements: $FeCl_3.6H_2O$ 1.5 μg/L, $CoCl_2.6H_2O$ 0.1 μg/L, $CuCl_2.2H_2O$ 0.1 μg/L, $ZnCl_2$ 0.1 μg/L, $Na_2MoO_4.2H_2O$ 0.1 μg/L, $MnCl_2.4H_2O_2$ 0.2 μg/L, and $H_3BO_3$ 0.05 μg/L.

Fermentation medium is the same as seed medium, supplemented with 50 g/L of glucose and 100 mM $KHCO_3$. The anaerobic fermentation of the strains Suc-T110, NZ-035, NZ-038, NZ-041, NZ-098, NZ-099 and NZ-100 was carried out as follows:

(a) Seed culture: 100 ml of seed medium in a 250 ml flask was sterilized at 115° C. for 15 min. The recombinant *E. coli* Suc-T110, NZ-035, NZ-038, NZ-041, NZ-098, NZ-099 and NZ-100 were grown by transferring pre-inocula into the seed medium with an inoculum of 1% (v/v), at 37° C. shaking with 100 rpm for 12 hours to obtain seed culture;

(b) Fermentation culture: the seed cultures were diluted into a 500-ml fermentation vessel containing 250 ml fermentation medium with a final concentration of $OD_{550}=0.1$. Fermentations were grown at 37° C., 150 rpm for 4 days. The neutralizer was a base containing 2.4 M potassium carbonate and 1.2 M potassium hydroxide. The fermentation broth comprises all the substance in the vessel. No air was sparged in whole processes for fermentation.

Analysis: the components in the fermentation broth were assayed on day 4 by using the High-Performance Liquid Chromatograph (Agilent-1200). The concentrations of glucose and organic acids in the fermentation broth were measured by the column of Aminex HPX-87H (Bio-rad).

The results were shown in Table 5. After 96 h fermentation, the strain Suc-T110 produced 280 mM of succinate with a yield of 1.12 mol/mol; after 96 h fermentation, the strain NZ-035 produced 286 mM of succinate with a yield of 1.16 mol/mol.

Using Suc-T110 as starting strain, the obtained recombinant *E. coli* strain NZ-099, with lpdA* integration and increasing its expression strength, produced 345 mM of succinate with a yield of 1.42 mol/mol after 96 h fermentation; comparing to NZ-035, the activity of pyruvate dehydrogenase under anaerobic condition was increased by 20-fold, and the titer of succinate was increased by 21%, and the yield of succinate was increased by 22%.

Using Suc-T110 as starting strain, by increasing the expression strength of aceEF gene, the obtained recombinant *E. coli* NZ-098 produced 302 mM of succinate with a yield of 1.23 mol/mol after 96 h fermentation; comparing to Suc-T110, the activity of pyruvate dehydrogenase under anaerobic condition was increased by 600 folds, and the titer of succinate was increased by 8%, and the yield of succinate was increased by 10%.

Using Suc-T110 as starting strain, the obtained recombinant *E. coli* NZ-100, with lpdA* integration and increasing the expression strength of lpdA* and aceEF genes, produced 353 mM of succinate with a yield of 1.45 mol/mol after 96 h fermentation; comparing to NZ-035, the activity of pyruvate dehydrogenase under anaerobic condition was increased by 580 folds, and the titer of succinate was increased by 23%, and the yield of succinate was increased by 25%.

TABLE 5

Production of succinate by fermentation of the strains Suc-T110, NZ-035, NZ-038, NZ-041, NZ-098, NZ-099, and NZ-100

| Strain | Genetic modification | Cell mass (g/L) | PDH activity (U/mg protein) | Succinate yield (mol/mol) | Fermentation product (mM) | |
|---|---|---|---|---|---|---|
| | | | | | succinate | acetate |
| Suc-T110 | | 1.53 | 0.013 ± 0.002 | 1.12 ± 0.03 | 280 ± 10 | 96 ± 10 |
| NZ-035 | Suc-T110, ΔackA-pta | 1.51 | 0.015 ± 0.001 | 1.16 ± 0.03 | 286 ± 7 | 44 ± 6 |
| NZ-038 | Suc-T110, ackA::M1-93-lpdA* | 1.36 | 0.285 ± 0.02 | 1.22 ± 0.04 | 304 ± 10 | 40 ± 5 |
| NZ-099 | Suc-T110, ackA::RBSL10-lpdA* | 1.58 | 0.30 ± 0.03 | 1.42 ± 0.02 | 345 ± 6 | 23 ± 4 |
| NZ-098 | Suc-T110, RBSL1-aceEF | 1.70 | 7.8 ± 0.2 | 1.23 ± 0.03 | 302 ± 8 | 15 ± 2 |
| NZ-041 | Suc-T110, M1-93-aceEF, ackA::M1-93-lpdA* | 1.40 | 0.8 ± 0.02 | 1.31 ± 0.03 | 319 ± 6 | 35 ± 6 |
| NZ-100 | Suc-T110, RBSL1-aceEF, ackA::RBSL10-lpdA* | 1.86 | 8.7 ± 0.3 | 1.45 ± 0.03 | 353 ± 8 | 21 ± 6 |

REFERENCES

Cassey B, Guest J R, Attwood M M (1998) Environmental control of pyruvate dehydrogenase complex expression in *Escherichia coli*. FEMS Microbiol Lett 159:325-329.

Bisswanger H. (1981) Substrate specificity of the pyruvate dehydrogenase complex from *Escherichia coli*. J Biol Chem 256: 815-822.

Garrigues C, Loubiere P, Lindley N D, Cocaign-Bousquet M (1997) Control of the shift from homolactic acid to mixed-acid fermentation in *Lactococcus lactis*: predominant role of the NADH/NAD ratio. J Bacteriol 179: 5282-5287.

Hansen H G, Henning U (1966) Regulation of pyruvate dehydrogenase activity in *Escherichia coli* K12. Biochim Biophys Acta 122: 355-358.

Kim Y, Ingram L O, Shanmugam K T (2008) Dihydrolipoamide dehydrogenase mutation alters the NADH sensitivity of pyruvate dehydrogenase complex of *Escherichia coli* K-12. J Bacteriol 190: 3851-3858.

Quail M A, Haydon D J, Guest J R (1994) The pdhR-aceEF-lpd operon of *Escherichia coli* expresses the pyruvate dehydrogenase complex. J Mol Microbiol 12:95-104.

Lu J, Tang J, Liu Y, Zhu X, Zhang T, Zhang X (2012) Combinatorial modulation of galP and glk gene expression for improved alternative glucose utilization. Appl Microbiol Biotechnol 93:2455-2426.

Shi A, Zhu X, Lu J, Zhang X, Ma Y (2013) Combinatorial activation of transhydrogenase and NAD kinase for improving isobutanol production. Metab Eng, 16:1-10.

Zhou S, Iverson A G, Grayburn W S (2008) Engineering a native homo ethanol pathway in *Escherichia coli* B for ethanol production. Biotechnol Lett 30:335-342.

Zhao J, Li Q, Sun T, Zhu X, Xu H, Tang J, Zhang X, Ma Y (2013) Engineering central metabolic modules of *Escherichia coli* for improving β-carotene production. Metab Eng 17:42-50.

---

The invention claimed is:

1. A recombinant *E. coli*, wherein said *E. coli* contains a mutated lpdA gene encoding lipoamide dehydrogenase, wherein the polypeptide encoded by the mutated lpdA gene consists of the amino acid sequence SEQ ID No.: 1 with a modification at position A358 of SEQ ID No.: 1 and optionally modification(s) at one or both positions T81 and P275, SEQ ID No.: 1,
  wherein the modification at the position T81, is the replacement of T with I; the modification at the position P275 is the replacement of P with S; and the modification at the position A358 is the replacement of A with V;
  optionally, the expression of the mutated lpdA gene, or the activity of the protein encoded by said mutated lpdA gene, in the recombinant *E. coli*, is enhanced.

2. The *E. coli* of claim 1, wherein said mutated lpdA gene consists of the nucleotide sequence SEQ ID No.: 2 with a mutation at position C1073 of SEQ ID No.: 2 and optionally at one or both positions of the positions C242 and C823, of SEQ ID No.: 2,
  optionally the mutation is the replacement of C with T.

3. The *E. coli* of claim 1, wherein the polypeptide encoded by said mutated lpdA gene consists of the amino acid sequence SEQ ID No.: 1 with the modifications at the positions T81, P275 and A358 of SEQ ID No.: 1.

4. The *E. coli* of claim 2, wherein said mutated lpdA gene consists of the nucleotide sequence SEQ ID No.: 2 with the mutation at the positions C242, C823 and C1073 of SEQ ID No.: 2.

5. The *E. coli* of claim 1, wherein said mutated lpdA gene is in a plasmid or a chromosome.

6. The *E. coli* of claim 1, wherein said *E. coli* also contains the modifications of:
  inhibited expression of the gene(s) involved in phosphoenolpyruvate:sugar phosphotransferase system (PTS), or inhibited activities of the protein(s) encoded by the gene(s) involved in phosphoenolpyruvate:sugar phosphotransferase system (PTS);
  inhibited expression of pflB or adhE genes, or inhibited activities of the protein(s) encoded by pflB and/or adhE genes;
  inhibited expression of ldhA gene, or inhibited activity of the protein encoded by ldhA gene;
  enhanced expression of galP gene or exogenous glf gene, or enhanced activities of the protein(s) encoded by galP gene or exogenous glf gene; and
  enhanced expression of pck gene, or enhanced activity of the protein encoded by pck gene,
  wherein the pflB encodes pyruvate formate lyase, the adhE gene encodes ethanol/acetaldehyde dehydrogenase, the ldhA gene encodes lactate dehydrogenase, the galP gene encodes galactose MFS transporter, the glf gene encodes glucose transporter Glf glucose facilitator protein), and the pck gene encodes phosphenolpyruvate carboxykinase.

7. The *E. coli* of claim 6, wherein said gene(s) involved in phosphoenolpyruvate:sugar phosphotransferase system (PTS) are one or more genes selected from the group consisting of genes ptsI encoding PTS system enzyme I, ptsH encoding PTS system enzyme Hpr, crr encoding PTS system enzyme IIA$^{Glc}$ and ptsG encoding PTS system enzyme IICB$^{Glc}$.

8. The *E. coli* of claim 1, wherein said *E. coli* also contains the genetic modifications of:

inhibited expression of pflB gene, or inhibited activity of the protein encoded by pflB gene;

inhibited expression of ldhA gene, or inhibited activity of the protein encoded by ldhA gene; and inhibited expression of frdABCD gene cluster, or inhibited activities of the protein(s) encoded by frdABCD gene cluster, wherein the frdABCD gene cluster encodes fumarate reductase, including frdA gene encoding fumarate reductase flavoprotein subunit, frdB gene encoding fumarate reductase iron-sulphur protein subunit, frdC gene encoding fumarate reductase subunit C and frdD gene encoding fumarate reductase subunit D.

9. The *E. coli* of claim 1, wherein said *E. coli* also contains the genetic modification of: enhanced expression of aceEF gene cluster, or enhanced activities of the protein(s) encoded by aceEF gene cluster, wherein the aceEF gene cluster encodes pyruvate complex E1/E2, including aceE gene encoding pyruvate dehydrogenase complex E1 and aceF gene encoding pyruvate dehydrogenase complex E2.

10. A method for producing ethanol and/or succinate, comprising culturing the *E. coli* of claim 1.

* * * * *

SEQUENCE LISTING

```
<160> NUMBER OF SEQ ID NOS: 82

<210> SEQ ID NO 1
<211> LENGTH: 474
<212> TYPE: PRT
<213> ORGANISM: Escherichia coli
<220> FEATURE:
<221> NAME/KEY: PEPTIDE
<222> LOCATION: (1)..(474)

<400> SEQUENCE: 1

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
                35                  40                  45

Gly Cys Ile Pro Ser Lys Ala Leu Leu His Val Ala Lys Val Ile Glu
            50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                    85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                    165                 170                 175

Arg Leu Leu Val Met Gly Gly Gly Ile Ile Gly Leu Glu Met Gly Thr
                180                 185                 190

Val Tyr His Ala Leu Gly Ser Gln Ile Asp Val Val Glu Met Phe Asp
            195                 200                 205

Gln Val Ile Pro Ala Ala Asp Lys Asp Ile Val Lys Val Phe Thr Lys
        210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                    245                 250                 255
```

```
Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Phe Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 2
<211> LENGTH: 1425
<212> TYPE: DNA
<213> ORGANISM: Escherichia coli
<220> FEATURE:
<221> NAME/KEY: gene
<222> LOCATION: (1)..(1425)

<400> SEQUENCE: 2
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta agcactgct gcacgtagca     180 aaagttatcg aagaagccaa agcgctggct gaacacggta tcgtcttcgg cgaaccgaaa     240
accgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctggaagt tgaaggtgag aacggcaaaa ccgtgatcaa cttcgacaac     420
gcgatcattg cagcgggttc tcgcccgatc caactgccgt ttattccgca tgaagatccg     480
cgtatctggg actccactga cgcgctgaaa ctgaaagaag taccagaacg cctgctggta     540
atgggtggcg gtatcatcgg tctggaaatg ggcaccgttt accacgcgct gggttcacag     600
attgacgtgg ttgaaatgtt cgaccaggtt atcccggcag ctgacaaaga catcgttaaa     660
gtcttcacca gcgtatcag caagaaattc aacctgatgc tggaaaccaa agttaccgcc     720
gttgaagcga agaagacgg catttatgtg acgatggaag gcaaaaaagc accgctgaa     780
```

```
ccgcagcgtt acgacgccgt gctggtagcg attggtcgtg tgccgaacgg taaaaaccct c    840 gacgcaggca aagcaggcgt ggaagttgac gaccgtggtt tcatccgcgt tgacaaacag      900
ctgcgtacca acgtaccgca catctttgct atcggcgata tcgtcggtca accgatgctg      960
gcacacaaag gtgttcacga aggtcacgtt gccgctgaag ttatcgccgg taagaaacac     1020
tacttcgatc cgaaagttat cccgtccatc gcctataccg aaccagaagt tgcatgggtg     1080
ggtctgacta gaaagaagc gaaagagaaa ggcatcagct atgaaaccgc caccttcccg      1140
```
(approximate — see rules)

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Ser Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Val Trp Val Gly Leu Thr Glu Lys Glu Ala Lys
        355                 360                 365

Glu Lys Gly Ile Ser Phe Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 4
<211> LENGTH: 1425
<212> TYPE: DNA
<213> ORGANISM: Escherichia coli
<220> FEATURE:
<221> NAME/KEY: gene
<222> LOCATION: (1)..(1425)

<400> SEQUENCE: 4

| | | | | | |
|---|---|---|---|---|---|
| atgagtactg | aaatcaaaac | tcaggtcgtg | gtacttgggg | caggccccgc | aggttactcc | 60 |
| gctgccttcc | gttgcgctga | tttaggtctg | gaaaccgtaa | tcgtagaacg | ttacaacacc | 120 |
| cttggcggtg | tttgcctgaa | cgtcggctgt | atcccttcta | aagcactgct | gcacgtagca | 180 |
| aaagttatcg | aagaagccaa | agcgctggct | gaacacggta | tcgtcttcgg | cgaaccgaaa | 240 |
| atcgatatcg | acaagattcg | tacctggaaa | gagaaagtga | tcaatcagct | gaccggtggt | 300 |
| ctggctggta | tggcgaaagg | ccgcaaagtc | aaagtggtca | acggtctggg | taaattcacc | 360 |
| ggggctaaca | ccctggaagt | tgaaggtgag | aacggcaaaa | ccgtgatcaa | cttcgacaac | 420 |
| gcgatcattg | cagcgggttc | tcgcccgatc | caactgccgt | ttattccgca | tgaagatccg | 480 |
| cgtatctggg | actccactga | cgcgctggaa | ctgaaagaag | taccagaacg | cctgctggta | 540 |
| atgggtggcg | gtatcatcgg | tctggaaatg | ggcaccgttt | accacgcgct | gggttcacag | 600 |
| attgacgtgt | tgaaatgtt | cgaccaggtt | atcccggcag | ctgacaaaga | catcgttaaa | 660 |
| gtcttcacca | agcgtatcag | caagaaattc | aacctgatgc | tggaaaccaa | agttaccgcc | 720 |

-continued

```
gttgaagcga aagaagacgg catttatgtg acgatggaag gcaaaaaagc acccgctgaa      780
ccgcagcgtt acgacgccgt gctggtagcg attggtcgtg tgtcgaacgg taaaaacctc      840
gacgcaggca aagcaggcgt ggaagttgac gaccgtggtt tcatccgcgt tgacaaacag      900
ctgcgtacca acgtaccgca catctttgct atcggcgata tcgtcggtca accgatgctg      960
gcacacaaag gtgttcacga aggtcacgtt gccgctgaag ttatcgccgg taagaaacac     1020
tacttcgatc cgaaagttat cccgtccatc gcctataccg aaccagaagt tgtatgggtg     1080
ggtctgactg agaagaagc gaaagagaaa ggcatcagct atgaaaccgc caccttcccg      1140
tgggctgctt ctggtcgtgc tatcgcttcc gactgcgcag acggtatgac caagctgatt     1200
ttcgacaaag aatctcaccg tgtgatcggt ggtgcgattg tcggtactaa cggcggcgag     1260
ctgctgggtg aaatcggcct ggcaatcgaa atgggttgtg atgctgaaga catcgcactg     1320
accatccacg cgcacccgac tctgcacgag tctgtgggcc tggcggcaga agtgttcgaa     1380
ggtagcatta ccgacctgcc gaacccgaaa gcgaagaaga agtaa                      1425
```

```
<210> SEQ ID NO 5
<211> LENGTH: 378
<212> TYPE: DNA
<213> ORGANISM: Artificial
<220> FEATURE:
<223> OTHER INFORMATION: Promoter
<220> FEATURE:
<221> NAME/KEY: promoter
<222> LOCATION: (1)..(378)

<400> SEQUENCE: 5
```

```
gttggttatc cagaatcaaa aggtgggtta attatcgcat ccgggcagta gtattttgct       60
tttttcagaa aataatcaaa aaaagttagc gtggtgaatc gatactttac cggttgaatt      120
tgcatcaatt tcattcagga atgcgattcc actcacaata ttcccgccat ataaaccaag      180
atttaacctt tgagaacat tttccacacc taaaatgcta tttctgcgat aatagcaacc      240
gtttcgtgac aggaatcacg gagttttttg tcaaatatga atttctccag atacgtaaat     300
ctatgagcct tgtcacggtt aacaccccca aaaagacttt actattcagg caatacatat     360
tggctaagga gcagtgaa                                                   378
```

```
<210> SEQ ID NO 6
<211> LENGTH: 88
<212> TYPE: DNA
<213> ORGANISM: Artificial
<220> FEATURE:
<223> OTHER INFORMATION: Promoter
<220> FEATURE:
<221> NAME/KEY: promoter
<222> LOCATION: (1)..(88)

<400> SEQUENCE: 6
```

```
ttatctctgg cggtgttgac aagagataac aacgttgata taattgagcc cgtattgtta      60
gcatgtacgt ttaaaccagg aaacagct                                         88
```

```
<210> SEQ ID NO 7
<211> LENGTH: 45
<212> TYPE: DNA
<213> ORGANISM: Artificial
<220> FEATURE:
<223> OTHER INFORMATION: primer

<400> SEQUENCE: 7
```

```
gcatgagctc aaggagatat accatgagta ctgaaatcaa aactc          45
```

<210> SEQ ID NO 8
<211> LENGTH: 35
<212> TYPE: DNA
<213> ORGANISM: Artificial
<220> FEATURE:
<223> OTHER INFORMATION: primer

<400> SEQUENCE: 8

```
gcatctgcag ttacttcttc ttcgctttcg ggttc                     35
```

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

```
gttgcatggg tgggtctgac                                      20
```

<210> SEQ ID NO 10
<211> LENGTH: 31
<212> TYPE: DNA
<213> ORGANISM: Artificial
<220> FEATURE:
<223> OTHER INFORMATION: primer

<400> SEQUENCE: 10

```
ttctggtttg gtataggcga tggacgggat a                         31
```

<210> SEQ ID NO 11
<211> LENGTH: 19
<212> TYPE: DNA
<213> ORGANISM: Artificial
<220> FEATURE:
<223> OTHER INFORMATION: primer

<400> SEQUENCE: 11

```
tcgacaagat tcgtacctg                                       19
```

<210> SEQ ID NO 12
<211> LENGTH: 26
<212> TYPE: DNA
<213> ORGANISM: Artificial
<220> FEATURE:
<223> OTHER INFORMATION: primer

<400> SEQUENCE: 12

```
tatcgatttt cggttcgcca aagacg                               26
```

<210> SEQ ID NO 13
<211> LENGTH: 19
<212> TYPE: DNA
<213> ORGANISM: Artificial
<220> FEATURE:
<223> OTHER INFORMATION: primer

<400> SEQUENCE: 13

```
ggtaaaaacc tcgacgcag                                       19
```

<210> SEQ ID NO 14
<211> LENGTH: 24
<212> TYPE: DNA
<213> ORGANISM: Artificial

```
<220> FEATURE:
<223> OTHER INFORMATION: primer

<400> SEQUENCE: 14
gttcgacaca cgaccaatcg ctac                                           24

<210> SEQ ID NO 15
<211> LENGTH: 24
<212> TYPE: DNA
<213> ORGANISM: Artificial
<220> FEATURE:
<223> OTHER INFORMATION: primer

<400> SEQUENCE: 15
gttgtatggg taggtctgac tgag                                           24

<210> SEQ ID NO 16
<211> LENGTH: 18
<212> TYPE: DNA
<213> ORGANISM: Artificial
<220> FEATURE:
<223> OTHER INFORMATION: primer

<400> SEQUENCE: 16
ttctggttcg gtataggc                                                  18

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
ttgcgccgac atcataac                                                  18

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
ctgcgttctg atttaatctg                                                20

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
gctaggtacc tgtgacggaa gatcacttcg                                     30

<210> SEQ ID NO 20
<211> LENGTH: 29
<212> TYPE: DNA
<213> ORGANISM: Artificial
<220> FEATURE:
<223> OTHER INFORMATION: primer

<400> SEQUENCE: 20
gctagagctc gcggctattt aacgaccct                                      29
```

<210> SEQ ID NO 21
<211> LENGTH: 29
<212> TYPE: DNA
<213> ORGANISM: Artificial
<220> FEATURE:
<223> OTHER INFORMATION: primer

<400> SEQUENCE: 21
gctagagctc aagtaaatcg cgcgggttt                             29

<210> SEQ ID NO 22
<211> LENGTH: 33
<212> TYPE: DNA
<213> ORGANISM: Artificial
<220> FEATURE:
<223> OTHER INFORMATION: primer

<400> SEQUENCE: 22
gctaggatcc ttatttgtta actgttaatt gtc                        33

<210> SEQ ID NO 23
<211> LENGTH: 17
<212> TYPE: DNA
<213> ORGANISM: Artificial
<220> FEATURE:
<223> OTHER INFORMATION: primer

<400> SEQUENCE: 23
gtaaaacgac ggccagt                                          17

<210> SEQ ID NO 24
<211> LENGTH: 17
<212> TYPE: DNA
<213> ORGANISM: Artificial
<220> FEATURE:
<223> OTHER INFORMATION: primer

<400> SEQUENCE: 24
caggaaacag ctatgac                                          17

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
gataacggag atcgggaatg                                       20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
ctttggctgt cagttcacca                                       20

<210> SEQ ID NO 27
<211> LENGTH: 20
<212> TYPE: DNA
<213> ORGANISM: Artificial
<220> FEATURE:
<223> OTHER INFORMATION: primer

```
<400> SEQUENCE: 27
tctggaaaaa ggcgaaacct                                        20

<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
tttgtgctat aaacggcgag t                                      21

<210> SEQ ID NO 29
<211> LENGTH: 22
<212> TYPE: DNA
<213> ORGANISM: Artificial
<220> FEATURE:
<223> OTHER INFORMATION: primer

<400> SEQUENCE: 29
tgtgacggaa gatcacttcg ca                                     22

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
ttatttgtta actgttaatt gtcct                                  25

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
tgtccgagct taatgaaaag tt                                     22

<210> SEQ ID NO 32
<211> LENGTH: 22
<212> TYPE: DNA
<213> ORGANISM: Artificial
<220> FEATURE:
<223> OTHER INFORMATION: primer

<400> SEQUENCE: 32
cgagtaataa cgtcctgctg ct                                     22

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
aaacgggtaa caccccagac                                        20

<210> SEQ ID NO 34
```

<211> LENGTH: 20
<212> TYPE: DNA
<213> ORGANISM: Artificial
<220> FEATURE:
<223> OTHER INFORMATION: primer

<400> SEQUENCE: 34
cggagtgtaa acgtcgaaca                                                   20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
tgcagaaaac catcgacaag                                                   20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
caccaatcag cgtgacaact                                                   20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
gccaccatcg taatcctgtt                                                   20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
atagcgcacc acctcaattt                                                   20

<210> SEQ ID NO 39
<211> LENGTH: 30
<212> TYPE: DNA
<213> ORGANISM: Artificial
<220> FEATURE:
<223> OTHER INFORMATION: primer

<400> SEQUENCE: 39
gcatttaatt aagtgtaggc tggagctgct                                        30

<210> SEQ ID NO 40
<211> LENGTH: 25
<212> TYPE: DNA
<213> ORGANISM: Artificial
<220> FEATURE:
<223> OTHER INFORMATION: primer

<400> SEQUENCE: 40

```
gcatgaattc cagaatcgaa atctc                                          25

<210> SEQ ID NO 41
<211> LENGTH: 19
<212> TYPE: DNA
<213> ORGANISM: Artificial
<220> FEATURE:
<223> OTHER INFORMATION: primer

<400> SEQUENCE: 41
ccgtgatatt gctgaagag                                                 19

<210> SEQ ID NO 42
<211> LENGTH: 87
<212> TYPE: DNA
<213> ORGANISM: Artificial
<220> FEATURE:
<223> OTHER INFORMATION: primer

<400> SEQUENCE: 42
tcatcatgcg ctacgctcta tggctccctg acgttttttt agccacgtat caattatagg    60
tacttccgtg taggctggag ctgcttc                                        87

<210> SEQ ID NO 43
<211> LENGTH: 83
<212> TYPE: DNA
<213> ORGANISM: Artificial
<220> FEATURE:
<223> OTHER INFORMATION: primer

<400> SEQUENCE: 43
gttaagcaag ataatcagaa aggattaatg cagattaaga gaataaaaaa ccggaaatag    60 tgaaaaggc catccgtcag gat                                             83

<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
agcagtgctt tagaagggat ac                                             22

<210> SEQ ID NO 45
<211> LENGTH: 89
<212> TYPE: DNA
<213> ORGANISM: Artificial
<220> FEATURE:
<223> OTHER INFORMATION: primer

<400> SEQUENCE: 45
tcatcatgcg ctacgctcta tggctccctg acgttttttt agccacgtat caattatagg    60
tacttcctgt gacggaagat cacttcgca                                      89

<210> SEQ ID NO 46
<211> LENGTH: 99
<212> TYPE: DNA
<213> ORGANISM: Artificial
<220> FEATURE:
<223> OTHER INFORMATION: primer

<400> SEQUENCE: 46
```

```
cggaaggcag cggagtaacc tgcggggcct gccccaagta ccacgacctg agttttgatt       60
tcagtactca tcatttattt gttaactgtt aattgtcct                              99

<210> SEQ ID NO 47
<211> LENGTH: 87
<212> TYPE: DNA
<213> ORGANISM: Artificial
<220> FEATURE:
<223> OTHER INFORMATION: primer

<400> SEQUENCE: 47
tcatcatgcg ctacgctcta tggctccctg acgttttttt agccacgtat caattatagg       60
tacttcctta tctctggcgg tgttgac                                           87

<210> SEQ ID NO 48
<211> LENGTH: 89
<212> TYPE: DNA
<213> ORGANISM: Artificial
<220> FEATURE:
<223> OTHER INFORMATION: primer

<400> SEQUENCE: 48
cggaaggcag cggagtaacc tgcggggcct gccccaagta ccacgacctg agttttgatt       60
tcagtactca tcatagctgt ttcctggtt                                         89

<210> SEQ ID NO 49
<211> LENGTH: 18
<212> TYPE: DNA
<213> ORGANISM: Artificial
<220> FEATURE:
<223> OTHER INFORMATION: primer

<400> SEQUENCE: 49
ccagccacca caatccct                                                     18

<210> SEQ ID NO 50
<211> LENGTH: 102
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (75)..(80)
<223> OTHER INFORMATION: n is a, c, g, or t

<400> SEQUENCE: 50
cggaaggcag cggagtaacc tgcggggcct gccccaagta ccacgacctg agttttgatt       60
tcagtactca tcatnnnnnn yctcctggtt taaacgtaca tg                         102

<210> SEQ ID NO 51
<211> LENGTH: 82
<212> TYPE: DNA
<213> ORGANISM: Artificial
<220> FEATURE:
<223> OTHER INFORMATION: primer

<400> SEQUENCE: 51
agacttccgt cagatcaaga ataatggtat gcggcagcga atgcacccgc tttatgcatg       60
tgtgacggaa gatcacttcg ca                                                82

<210> SEQ ID NO 52
<211> LENGTH: 83
```

```
<212> TYPE: DNA
<213> ORGANISM: Artificial
<220> FEATURE:
<223> OTHER INFORMATION: primer

<400> SEQUENCE: 52
cctggagcca gtcgcgagtt tcgatcggat ccacgtcatt tgggaaacgt tctgacattt      60
atttgttaac tgttaattgt cct                                             83

<210> SEQ ID NO 53
<211> LENGTH: 80
<212> TYPE: DNA
<213> ORGANISM: Artificial
<220> FEATURE:
<223> OTHER INFORMATION: primer

<400> SEQUENCE: 53
agacttccgt cagatcaaga ataatggtat gcggcagcga atgcacccgc tttatgcatg      60
ttatctctgg cggtgttgac                                                 80

<210> SEQ ID NO 54
<211> LENGTH: 70
<212> TYPE: DNA
<213> ORGANISM: Artificial
<220> FEATURE:
<223> OTHER INFORMATION: primer

<400> SEQUENCE: 54
cctggagcca gtcgcgagtt tcgatcggat ccacgtcatt tgggaaacgt tctgacatag      60
ctgtttcctg                                                            70

<210> SEQ ID NO 55
<211> LENGTH: 24
<212> TYPE: DNA
<213> ORGANISM: Artificial
<220> FEATURE:
<223> OTHER INFORMATION: primer

<400> SEQUENCE: 55
acggaagaag tggttaaagc acac                                            24

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
ttatctctgg cggtgttgac                                                 20

<210> SEQ ID NO 57
<211> LENGTH: 80
<212> TYPE: DNA
<213> ORGANISM: Artificial
<220> FEATURE:
<223> OTHER INFORMATION: primer

<400> SEQUENCE: 57
agacttccgt cagatcaaga ataatggtat gcggcagcga atgcacccgc tttatgcatg      60
gtgtaggctg gagctgcttc                                                 80

<210> SEQ ID NO 58
```

```
<211> LENGTH: 86
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (59)..(64)
<223> OTHER INFORMATION: n is a, c, g, or t

<400> SEQUENCE: 58
cctggagcca gtcgcgagtt tcgatcggat ccacgtcatt tgggaaacgt tctgacatnn      60
nnnnyctcct ggtttaaacg tacatg                                          86

<210> SEQ ID NO 59
<211> LENGTH: 18
<212> TYPE: DNA
<213> ORGANISM: Artificial
<220> FEATURE:
<223> OTHER INFORMATION: primer

<400> SEQUENCE: 59
aagggcttgt tgcttcgt                                                   18

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
cgcattatgt tcccgatgat                                                 20

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
gcctttcagt tcaacggtgt                                                 20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
cggcccaatt tactgcttag                                                 20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
atccccagca acagaagtgt                                                 20

<210> SEQ ID NO 64
<211> LENGTH: 20
```

```
<212> TYPE: DNA
<213> ORGANISM: Artificial
<220> FEATURE:
<223> OTHER INFORMATION: primer

<400> SEQUENCE: 64
atctgctgca cccgatctac                                          20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
gaaccggcaa caaacaaaat                                          20

<210> SEQ ID NO 66
<211> LENGTH: 23
<212> TYPE: DNA
<213> ORGANISM: Artificial
<220> FEATURE:
<223> OTHER INFORMATION: primer

<400> SEQUENCE: 66
atgcctgacg ctaaaaaaca ggg                                      23

<210> SEQ ID NO 67
<211> LENGTH: 22
<212> TYPE: DNA
<213> ORGANISM: Artificial
<220> FEATURE:
<223> OTHER INFORMATION: primer

<400> SEQUENCE: 67
gattaaacgc tgttatctgc aa                                       22

<210> SEQ ID NO 68
<211> LENGTH: 30
<212> TYPE: DNA
<213> ORGANISM: Artificial
<220> FEATURE:
<223> OTHER INFORMATION: primer

<400> SEQUENCE: 68
gcatactagt gttggttatc cagaatcaaa                               30

<210> SEQ ID NO 69
<211> LENGTH: 34
<212> TYPE: DNA
<213> ORGANISM: Artificial
<220> FEATURE:
<223> OTHER INFORMATION: primer

<400> SEQUENCE: 69
gcatggtacc agccaatatg tattgcctga atag                          34

<210> SEQ ID NO 70
<211> LENGTH: 21
<212> TYPE: DNA
<213> ORGANISM: Artificial
<220> FEATURE:
<223> OTHER INFORMATION: primer

<400> SEQUENCE: 70
```

```
acggttaaca cccccaaaaa g                                                    21
```

<210> SEQ ID NO 71
<211> LENGTH: 25
<212> TYPE: DNA
<213> ORGANISM: Artificial
<220> FEATURE:
<223> OTHER INFORMATION: primer

<400> SEQUENCE: 71

```
gacaaggctc atagatttac gtatc                                                25
```

<210> SEQ ID NO 72
<211> LENGTH: 72
<212> TYPE: DNA
<213> ORGANISM: Artificial
<220> FEATURE:
<223> OTHER INFORMATION: primer

<400> SEQUENCE: 72

```
cgccatataa accaagattt aaccttttga gaacattttc cacacctaag tgtgacggaa           60
gatcacttcg ca                                                              72
```

<210> SEQ ID NO 73
<211> LENGTH: 75
<212> TYPE: DNA
<213> ORGANISM: Artificial
<220> FEATURE:
<223> OTHER INFORMATION: primer

<400> SEQUENCE: 73

```
ataccataag cctcgagttc ttgcggggtc aaaccattgt taacgcgcat ttatttgtta           60
actgttaatt gtcct                                                           75
```

<210> SEQ ID NO 74
<211> LENGTH: 18
<212> TYPE: DNA
<213> ORGANISM: Artificial
<220> FEATURE:
<223> OTHER INFORMATION: primer

<400> SEQUENCE: 74

```
acgccataaa caatccaa                                                        18
```

<210> SEQ ID NO 75
<211> LENGTH: 18
<212> TYPE: DNA
<213> ORGANISM: Artificial
<220> FEATURE:
<223> OTHER INFORMATION: primer

<400> SEQUENCE: 75

```
cgcatttcac tgctcctt                                                        18
```

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76

```
cgggacaacg ttcaaaacat                                                      20
```

```
<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
attgcccatc ttcttgttgg                                              20

<210> SEQ ID NO 78
<211> LENGTH: 21
<212> TYPE: DNA
<213> ORGANISM: Artificial
<220> FEATURE:
<223> OTHER INFORMATION: primer

<400> SEQUENCE: 78
aactaccgca gttcagaacc a                                            21

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
tctgaacacc ggtaacacca                                              20

<210> SEQ ID NO 80
<211> LENGTH: 89
<212> TYPE: DNA
<213> ORGANISM: Artificial
<220> FEATURE:
<223> OTHER INFORMATION: rbs regulatory element

<400> SEQUENCE: 80
ttatctctgg cggtgttgac aagagataac aacgttgata taattgagcc cgtattgtta    60
gcatgtacgt ttaaaccagg agaatcttg                                     89

<210> SEQ ID NO 81
<211> LENGTH: 89
<212> TYPE: DNA
<213> ORGANISM: Artificial
<220> FEATURE:
<223> OTHER INFORMATION: RBS regulatory element

<400> SEQUENCE: 81
ttatctctgg cggtgttgac aagagataac aacgttgata taattgagcc cgtattgtta    60
gcatgtacgt ttaaaccagg aggcacacc                                     89

<210> SEQ ID NO 82
<211> LENGTH: 3749
<212> TYPE: DNA
<213> ORGANISM: Artificial
<220> FEATURE:
<223> OTHER INFORMATION: Plasmid

<400> SEQUENCE: 82
gtttgacagc ttatcatcga ctgcacggtg caccaatgct tctggcgtca ggcagccatc    60
ggaagctgtg gtatggctgt gcaggtcgta aatcactgca taattcgtgt cgctcaaggc   120
gcactcccgt tctggataat gttttttgcg ccgacatcat aacggttctg gcaaatattc   180
```

-continued

```
tgaaatgagc tgttgacaat taatcatccg gctcgtataa tgtgtggaat tgtgagcgga      240
taacaatttc acacaggaaa cagaccatgg aattcgagct cggtacccgg ggatcctcta      300
gagtcgacct gcaggcatgc aagcttggct gttttggcgg atgagagaag attttcagcc      360
tgatacagat taaatcagaa cgcagaagcg gtctgataaa acagaatttg cctggcggca      420
gtagcgcggt ggtcccacct gaccccatgc cgaactcaga agtgaaacgc cgtagcgccg      480
atggtagtgt ggggtctccc catgcgagag tagggaactg ccaggcatca aataaaacga      540
aaggctcagt cgaaagactg ggcctttcgt tttatctgtt gtttgtcggt gaacgctctc      600
ctgagtagga caaatccgcc gggagcggat ttgaacgttg cgaagcaacg gcccggaggg      660
tggcgggcag gacgcccgcc ataaactgcc aggcatcaaa ttaagcagaa ggccatcctg      720
acggatggcc ttttttgcgtt tctttaatta aattcaaata tgtatccgct catgagacaa      780
taaccctgat aaatgcttca ataatattga aaaggaaga gtatgagtat tcaacatttc      840
cgtgtcgccc ttattccctt ttttgcggca ttttgccttc ctgttttgc tcacccagaa      900 acgctggtga agtaaaaga tgctgaagat cagttgggtg cacgagtggg ttacatcgaa      960
ctggatctca acagcggtaa gatccttgag agttttcgcc ccgaagaacg ttttccaatg     1020
atgagcactt ttaaagttct gctatgtggc gcggtattat cccgtgttga cgccgggcaa     1080
gagcaactcg gtcgccgcat acactattct cagaatgact tggttgagta ctcaccagtc     1140
acagaaaagc atcttacgga tggcatgaca gtaagagaat tatgcagtgc tgccataacc     1200
atgagtgata acactgcggc caacttactt ctgacaacga tcggaggacc gaaggagcta     1260
accgcttttt tgcacaacat gggggatcat gtaactcgcc ttgatcgttg gaaccggag      1320 ctgaatgaag ccataccaaa cgacgagcgt gacaccacga tgcctacagc aatggcaaca     1380
acgttgcgca aactattaac tggcgaacta cttactctag cttcccggca acaattaata     1440
gactggatgg aggcggataa agttgcagga ccacttctgc gctcggccct tccggctggc     1500
tggtttattg ctgataaatc tggagccggt gagcgtgggt ctcgcggtat cattgcagca     1560
ctggggccag atggtaagcc ctcccgtatc gtagttatct acacgacggg gagtcaggca     1620
actatggatg aacgaaatag acagatcgct gagataggtg cctcactgat taagcattgg     1680
taactgtcag accaagttta ctcatatata ctttagattg atttaaaact tcatttttaa     1740
tttaaaagga tctaggtgaa gatcctttt gataatctca tgaccaaaat cccttaacgt     1800
gagttttcgt tccactgagc gtcagacccc gtagaaaaga tcaaaggatc ttcttgagat     1860
cctttttttc tgcgcgtaat ctgctgcttg caaacaaaaa aaccaccgct accagcggtg     1920
gtttgtttgc cggatcaaga gctaccaact ctttttccga aggtaactgg cttcagcaga     1980
gcgcagatac caaatactgt ccttctagtg tagccgtagt taggccacca cttcaagaac     2040
tctgtagcac cgcctacata cctcgctctg ctaatcctgt taccagtggc tgctgccagt     2100
ggcgataagt cgtgtcttac cgggttggac tcaagacgat agttaccgga taaggcgcag     2160
cggtcgggct gaacggggggg ttcgtgcaca cagcccagct tggagcgaac gacctacacc     2220
gaactgagat acctacagcg tgagctatga gaaagcgcca cgcttcccga agggagaaag     2280
gcggacaggt atccggtaag cggcagggtc ggaacaggag agcgcacgag ggagcttcca     2340
gggggaaacg cctggtatct ttatagtcct gtcgggtttc gccacctctg acttgagcgt     2400
cgatttttgt gatgctcgtc agggggggcgg agcctatgga aaaacgccag caacgcggcc     2460 ttttttacggt tcctggcctt ttgctggcct tttgctcaca tgttctttcc tgcgttaatt     2520
aactagtcat atgggcatgc atttacgttg acaccatcga atggtgcaaa acctttcgcg     2580
```

```
gtatggcatg atagcgcccg gaagagagtc aattcagggt ggtgaatgtg aaaccagtaa    2640
cgttatacga tgtcgcagag tatgccggtg tctcttatca gaccgtttcc cgcgtggtga    2700
accaggccag ccacgtttct gcgaaaacgc gggaaaaagt ggaagcggcg atggcggagc    2760
tgaattacat tcccaaccgc gtggcacaac aactggcggg caaacagtcg ttgctgattg    2820
gcgttgccac ctccagtctg gccctgcacg cgccgtcgca aattgtcgcg gcgattaaat    2880
ctcgcgccga tcaactgggt gccagcgtgg tggtgtcgat ggtagaacga agcggcgtcg    2940
aagcctgtaa agcggcggtg cacaatcttc tcgcgcaacg cgtcagtggg ctgatcatta    3000
actatccgct ggatgaccag gatgccattg ctgtggaagc tgcctgcact aatgttccgg    3060
cgttatttct tgatgtctct gaccagacac ccatcaacag tattattttc tcccatgaag    3120
acggtacgcg actgggcgtg gagcatctgg tcgcattggg tcaccagcaa atcgcgctgt    3180
tagcgggccc attaagttct gtctcggcgc gtctgcgtct ggctggctgg cataaatatc    3240
tcactcgcaa tcaaattcag ccgatagcgg aacgggaagg cgactggagt gccatgtccg    3300
gttttcaaca aaccatgcaa atgctgaatg agggcatcgt tcccactgcg atgctggttg    3360
ccaacgatca gatggcgctg ggcgcaatgc gcgccattac cgagtccggg ctgcgcgttg    3420
gtgcggatat ctcggtagtg ggatacgacg ataccgaaga cagctcatgt tatatcccgc    3480
cgttaaccac catcaaacag gattttcgcc tgctggggca aaccagcgtg gaccgcttgc    3540
tgcaactctc tcagggccag gcggtgaagg gcaatcagct gttgcccgtc tcactggtga    3600
aaagaaaaac caccctggcg cccaatacgc aaaccgcctc tccccgcgcg ttggccgatt    3660
cattaatgca gctggcacga caggtttccc gactggaaag cgggcagtga gcgcaacgca    3720
attaatgtga gttagcgcga attgatctg                                      3749
```